(12) United States Patent
Fortte et al.

(10) Patent No.: US 7,820,822 B2
(45) Date of Patent: Oct. 26, 2010

(54) METAL COMPLEXES

(75) Inventors: Rocco Fortte, Frankfurt (DE); Philipp Stössel, Frankfurt (DE); Anja Gerhard, Darmstadt (DE); Horst Vestweber, Gilserberg-Winterscheid (DE)

(73) Assignee: Merck Patent GmbH (DE)

( * ) Notice: Subject to any disclaimer, the term of this patent is extended or adjusted under 35 U.S.C. 154(b) by 1107 days.

(21) Appl. No.: 10/573,931

(22) PCT Filed: Sep. 28, 2004

(86) PCT No.: PCT/EP2004/010836

§ 371 (c)(1),
(2), (4) Date: Aug. 15, 2006

(87) PCT Pub. No.: WO2005/033244

PCT Pub. Date: Apr. 14, 2005

(65) Prior Publication Data

US 2007/0034863 A1    Feb. 15, 2007

(30) Foreign Application Priority Data

Sep. 29, 2003    (DE) ............................ 103 45 572

(51) Int. Cl.
C07F 15/00    (2006.01)
H01L 51/50    (2006.01)
C07D 221/18    (2006.01)
(52) U.S. Cl. ............................ 546/10; 428/689; 546/75
(58) Field of Classification Search ............... 546/10, 546/75; 428/689
See application file for complete search history.

(56) References Cited

U.S. PATENT DOCUMENTS 4,128,650 A    12/1978    Fabre et al.
4,461,895 A    7/1984    Fritschi et al.

FOREIGN PATENT DOCUMENTS

EP    1 348 711 A1    1/2003

*Primary Examiner*—Charanjit S Aulakh
(74) *Attorney, Agent, or Firm*—Connolly Bove Lodge & Hutz LLP

(57) ABSTRACT

The present invention describes new types of metal complexes. Such compounds can be used as functional materials in a series of different types of applications which can be classified within the electronics industry in the widest sense.

The inventive compounds are described by the formulae (1) and (4).

19 Claims, 1 Drawing Sheet

Figure 1: Lifetime comparison of devices produced with the inventive dopant Ir1 and the comparative dopant Ir(piq)$_3$
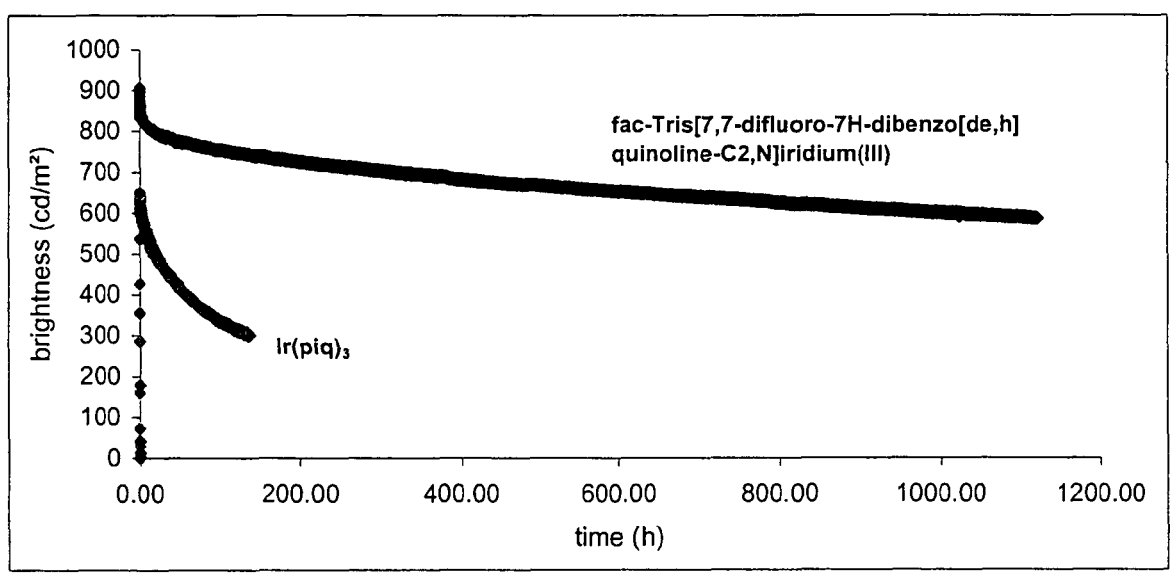

METAL COMPLEXES

RELATED APPLICATIONS

This application is the U.S. National Stage of International Application No. PCT/EP2004/010836, filed Sep. 28, 2004, published in German, and claims priority under 35 U.S.C. §119 or 365 to German Application No. 103 45 572.8, filed Sep. 29, 2003.

DESCRIPTION

The present invention relates to the use of novel materials and material mixtures in organic electronic devices such as electroluminescent elements, and to their use in displays based thereon.

In a series of different types of applications which can be classified within the electronics industry in the widest sense, the use of organic semiconductors as functional materials has become reality in recent times or is expected in the near future. For instance, light-sensitive organic materials (e.g. phthalocyanines) and organic charge transport materials (generally triarylamine-based hole transporters) have already found use for several years in copying machines. The use of specific semiconducting organic compounds, some of which are also capable of emission of light in the visible spectral region, is just starting to be introduced onto the market, for example in organic electroluminescent devices. Their individual components, the organic light-emitting diodes (OLEDs), have a very wide spectrum of application as:

1. white or colored backlighting for monochrome or multicolor display elements (for example in pocket calculators, for mobile telephones and other portable applications),
2. large-surface area displays (for example traffic signs, billboards, etc.),
3. illumination elements in all colors and forms,
4. monochrome or full-color passive matrix displays for portable applications (for example mobile telephones, PDAs, camcorders, etc.),
5. full-color, large-surface area, high-resolution active matrix displays for a wide variety of applications (for example mobile telephones, PDAs, laptops, televisions, etc.).

The development of some of these applications is already very far advanced. For instance, devices containing simple OLEDs have already been introduced onto the market, as demonstrated by the car radios from Pioneer or a digital camera from Kodak with an organic display; nevertheless, there is still great need for technical improvements.

A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, Appl. Phys. Lett. 1999, 75, 4-6]. For quantum-mechanical reasons, up to four times the quantum efficiency, energy efficiency and power efficiency are possible using organometallic compounds. Whether this new development will establish itself firstly depends strongly upon whether corresponding device compositions can be found which can also utilize these advantages (triplet emission=phosphorescence compared to singlet emission=fluorescence) in OLEDs. The essential conditions for practical use here are in particular a high operative lifetime, a high stability against thermal stress and a low use and operating voltage in order to enable mobile applications.

The general structure of organic electroluminescent devices is described, for example, in U.S. Pat. No. 4,539,507 and U.S. Pat. No. 5,151,629.

Typically, an organic electroluminescent device consists of a plurality of layers which are applied to one another by means of vacuum methods or various printing methods. These layers are specifically:
1. A carrier plate=substrate (typically glass or plastics film).
2. A transparent anode (typically indium tin oxide, ITO).
3. A hole injection layer (Hole Injection Layer=HIL): for example based on copper phthalocyanine (CuPc) or conductive polymers such as polyaniline (PANI) or polythiophene derivatives (such as PEDOT).
4. One or more hole transport layers (Hole Transport Layer=HTL): typically based on triarylamine derivatives, for example 4,4',4"-tris(N-1-naphthyl-N-phenylamino)triphenylamine(NaphDATA) as the first layer and N,N'-di(naphth-1-yl)-N,N'-diphenylbenzidine (NPB) as the second hole transport layer.
5. One or more emission layers (Emission Layer=EML): this layer (or layers) may coincide partly with layers 4 to 8, but consists typically of matrix materials, such as 4,4'-bis(carbazol-9-yl)biphenyl (CBP), doped with phosphorescent dyes, for example tris(2-phenylpyridyl)iridium (Ir(PPy)$_3$) or tris(2-benzothenylpyridyl)iridium (Ir(BTP)$_3$); however, the emission layer may also consist of polymers, mixtures of polymers, mixtures of polymers and low molecular weight compounds or mixtures of different low molecular weight compounds.
6. A hole blocking layer (Hole Blocking Layer=HBL): this layer may coincide partly with layers 7 and 8. It consists typically of BCP (2,9-dimethyl-4,7-diphenyl-1,10-phenanthroline=bathocuproin) or bis(2-methyl-8-quinolinolato)(4-phenylphenolato)aluminum(III) (BAlq).
7. An electron transport layer (Electron Transport Layer=ETL): usually based on aluminum tris-8-hydroxyquinolinate (AlQ$_3$).
8. An electron injection layer (Electron Injection Layer=EIL): a thin layer consisting of a material with a high dielectric constant, for example LiF, Li$_2$O, BaF$_2$, MgO, NaF.
9. A cathode: here, generally metals, metal combinations or metal alloys having a low work function are used, for example Ca, Ba, Cs, Mg, Al, In or Mg/Ag.

However, there are still considerable problems which are in need of urgent improvement in OLEDs which exhibit triplet emission. This is also especially true of the triplet emitter itself.

In the literature, emitters based on metal complexes have recently been described (for example US 2003/0068526, WO 2003/000661, EP 1211257), which contain iridium-coordinated 1-phenylisoquinoline ligands as part-structures of the formula A and formula B. The part-structures shown differ by the absence (formula A) and presence (formula B) of a bridge between the phenyl and the isoquinoline ring. The bridge contains 2-20 alkyl bridge carbon atoms which may optionally be replaced by heteroatoms.

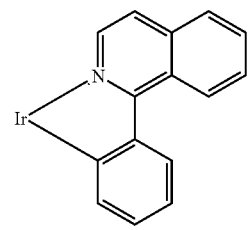

Formula A

-continued

Formula B

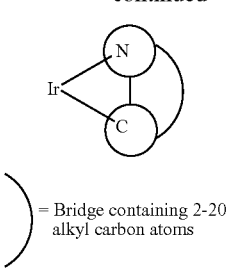

⎫
⎬ = Bridge containing 2-20 alkyl carbon atoms
⎭

In practice, compounds of this type have some weaknesses which make the industrial use of these compounds appear improbable:
1. They frequently have only a low solubility in organic solvents, which greatly hinders or even prevents efficient purification by recrystallization or chromatography. This applies especially to the purification of relatively large amounts, as are required in display manufacture.
2. In solution in particular, they are very oxidation-sensitive. In some cases, these compounds have to be purified, stored, transported and processed under inert gas.
3. A further crucial failing is the low thermal stability of the above-described compounds. For example, the homoleptic complex fac-tris(1-phenylisoquinoline-$C^2$,N)iridium(III), known in the relevant literature generally as Ir(piq)$_3$, cannot be sublimed without decomposition. Even under typical high-vacuum conditions (p<$10^{-7}$ mbar), considerable decomposition of this compound is observed with not only an iridium-containing ash which makes up approx. 30% by weight of the amount of fac-tris(1-phenylisoquinoline-$C^2$,N)iridium(III) but also the release of 1-phenylisoquinoline in addition to other low molecular weight compounds being detectable. This thermal decomposition leads to device characteristics with low reproducibility, the lifetime being particularly adversely affected.

It has now been found that, surprisingly, compounds which have a bond of the phenyl ring to the isoquinoline ring via a one-atom bridge have outstanding properties as triplet emitters in OLEDs.
1. The inventive compounds feature good solubility in organic solvents, which considerably eases their purification by common processes such as recrystallization or chromatography. This makes the compounds processible also from solution by coating or printing techniques. This property is also advantageous in the customary processing by evaporation, since the cleaning of the units and of the shadow masks used is thus considerably eased.
2. The inventive compounds feature improved oxidation stability, which has a positive effect on the purification and generally on the handling of these compounds. In addition, this can lead to a distinct increase in the operative lifetime in the case of use in corresponding inventive devices.
3. The inventive compounds also feature high thermal stability, so that they can generally be evaporated under high vacuum without decomposition. This property is a basic prerequisite for the reproducible preparation of OLEDs and has an especially positive effect on the operative lifetime. Moreover, the resource-protective utilization of compounds of these rare metals is thus possible.
4. The inventive compounds can be prepared very reproducibly in reliable high purity and have no batch variation. An industrial process for producing the inventive electroluminescent devices is therefore substantially more effective.

The present invention provides the compounds of the formula (1)

$$M(L)_n(L')_m(L'')_o$$  Formula (1)

containing a part-structure $M(L)_n$ of the formula (2)

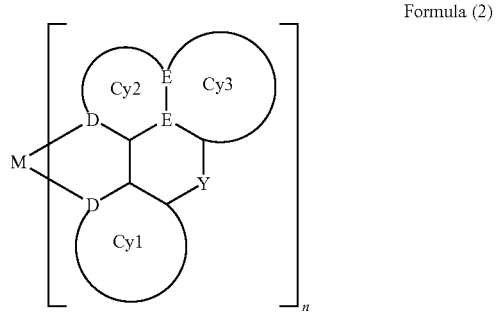

Formula (2)

where the symbols and indices used are:

M at each instance is a transition metal ion;

Y is the same or different at each instance and is $BR^1$, $CR_2$, C=O, C=$NR^1$, C=$CR_2$, $SiR^1_2$, $NR^1$, $PR^1$, $AsR^1$, $SbR^1$, $BiR^1$, $P(O)R^1$, $P(S)R^1$, $P(Se)R^1$, $As(O)R^1$, $As(S)R^1$, $As(Se)R^1$, $Sb(O)R^1$, $Sb(S)R^1$, $Sb(Se)R^1$, $Bi(O)R^1$, $Bi(S)R^1$, $Bi(Se)R^1$, O, S, Se, Te, SO, SeO, TeO, $SO_2$, $SeO_2$, $TeO_2$ or a single bond;

D is the same or different at each instance and is a carbon atom or a heteroatom with a nonbonding electron pair which coordinates to the metal, with the proviso that one D per ligand is a carbon atom and the other is a heteroatom with a nonbonding electron pair;

E is the same or different at each instance and is C or N, with the proviso that at least one symbol E is C;

Cy1 is the same or different at each instance and is a saturated, unsaturated or aromatic homo- or heterocycle which is bonded to the metal M via an atom D and which also has a single bond to the part-cycle Cy2 and a single bond to the Y group;

Cy2 is the same or different at each instance and is a saturated, unsaturated or aromatic part-homo- or -heterocycle which is bonded via an atom D to the metal M and which also has a single bond to the cycle Cy1 and a common edge with the part-cycle Cy3;

Cy3 is the same or different at each instance and is a saturated, unsaturated or aromatic part-homo- or -heterocycle which has a single bond to the Y group and a common edge with the part-cycle Cy2;

$R^1$ is the same or different at each instance and is H or an aliphatic or aromatic hydrocarbon radical having from 1 to 20 carbon atoms;

n is 1, 2 or 3;

the ligands L' and L'' in formula (1) are monoanionic, bidentate chelating ligands, and m and o are the same or different at each instance and are 0, 1 or 2.

Preference is given to compounds of the formula (1) containing a part-structure $M(L)_n$ of the formula (2a)

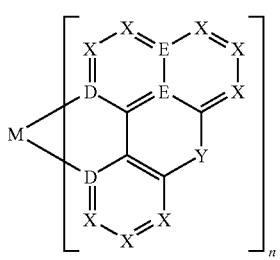

Formula (2a)

where Y, $R^1$, L', L" and n are each defined as described above, and the further symbols are:

M is Mo, W, Re, Ru, Os, Rh, Ir, Pd, Pt or Au;

D is the same or different at each instance and is a carbon atom, a nitrogen atom or a phosphorus atom, with the proviso that one D is a carbon atom and the other D is a nitrogen atom or a phosphorus atom;

X is the same or different at each instance and is CR, N or P; or one or more X-X units (i.e. two adjacent X) are NR, S or O; or one X-X unit (i.e. two adjacent X) in the fused part-cycles Cy2 and Cy3 is CR, N or P if one of the symbols E is N;

E is the same or different at each instance and is C or N, with the proviso that at least one symbol E is C and also with the proviso that precisely one X-X unit (i.e. two adjacent X) in the fused part-cycles Cy2 and Cy3 is CR, N or P if one symbol E is N;

R is the same or different at each instance and is H, F, Cl, Br, I, OH, $NO_2$, CN, a straight-chain, branched or cyclic alkyl or alkoxy group having from 1 to 20 carbon atoms, where one or more nonadjacent $CH_2$ groups may be replaced by $-R^1C=CR^1-$, $-C\equiv C-$, $Si(R^1)_2$, $Ge(R^1)_2$, $Sn(R^1)_2$, $-O-$, $-S-$, $-NR^1-$, $-(C=O)-$, $-(C=NR^1)-$, $-P=O(R^1)-$ or $-CONR^1-$ and where one or more hydrogen atoms may be replaced by F, or an aryl, heteroaryl, aryloxy or heteroaryloxy group which has from 1 to 14 carbon atoms and may be substituted by one or more nonaromatic R radicals, where a plurality of substituents R, both on the same ring and on different rings, may in turn form a further mono- or polycyclic, aliphatic or aromatic ring system.

A preferred embodiment of the present invention is that of the compounds of the formula (1a)

$$M(L)_n(L')_m(L'')_o \quad \text{Formula (1a)}$$

containing at least one part-structure $M(L)_n$ of the formula (2b), identically or differently at each instance,

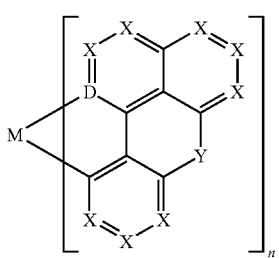

Formula (2b)

and optionally containing a part-structure $M(L')_m$ of the formula (3), identically or differently at each instance

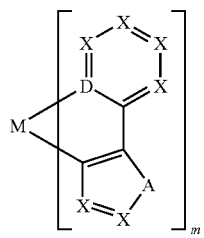

Formula (3)

where M, X, Y, R, $R^1$, L", n, m and o are each defined as described above, and the further symbols and indices are each defined as follows:

D is the same or different at each instance and is N or P;

A is the same or different at each instance and is $-CR=CR-$, $-N=CR-$, $-P=CR-$, $-N=N-$, $-P=N-$, NR, PR, O, S, Se.

Inventive monoanionic, bidentate ligands L" are 1,3-diketonates derived from 1,3-diketones, for example acetylacetone, benzoylacetone, 1,5-diphenylacetylacetone, bis(1,1,1-trifluoroacetyl)methane, 3-ketonates derived from 3-keto esters, for example ethyl acetoacetate, carboxylates derived from aminocarboxylic acids, for example pyridine-2-carboxylic acid, quinoline-2-carboxylic acid, glycine, N,N-dimethylglycine, alanine, N,N-dimethylalanine, salicyliminates derived from salicylimines, for example methylsalicylimine, ethylsalicylimine, phenylsalicylimine, borates of nitrogen-containing heterocycles, for example tetrakis(1-imidazolyl)borate and tetrakis(1-pyrazolyl)borate.

The inventive compounds are preferably of the formula (1) or formula (1a) in which the symbol M=Rh, Ir, Pd or Pt; more preferably, M=Ir or Pt.

Preference is likewise given to the inventive compounds of the formula (1) or formula (1a) in which the symbol n=2 or 3. Particular preference is given to compounds in which the symbol m=o=0. It is especially true that n=2 and m=o=0 for palladium and platinum complexes, and n=3 and m=o=0 for rhodium and iridium complexes.

Preference is given to the inventive compounds of the formula (1) or formula (1a) in which the symbol D=N.

Preference is given to the inventive compounds of the formula (1) or formula (1a) in which the symbol X=CR.

Preference is given to the inventive compounds of the formula (1) or (1a) in which the symbol Y=$CR_2$, C=O, C=$CR_2$, $NR^1$, $PR^1$, $P(O)R^1$, O, S, SO, $SO_2$ or a single bond. The symbol Y is more preferably $CR_2$.

Preference is likewise given to the inventive compounds of the formula (1) or formula (1a) in which the symbol R is:

R is the same or different at each instance and is H, F, a straight-chain, branched or cyclic alkyl or alkoxy group having from 1 to 4 carbon atoms, where one or more hydrogen atoms may be replaced by F, or an aryl or heteroaryl group which has from 1 to 6 carbon atoms and may be substituted by one or more nonaromatic R radicals, where a plurality of substituents R, both on the same ring and on different rings, together may in turn form a further aliphatic or aromatic, mono- or polycyclic ring system.

Even though it is already apparent from the statements already made above, it should be pointed out here explicitly once more that, in the case that Y=$CR_2$, the two substituents R may form a further aliphatic or aromatic, mono- or polycyclic ring system. In this case, the bridging carbon atom becomes the spiro carbon atom which bonds two ring systems orthogonally to one another.

In accordance with the statement made above, preference is likewise given to compounds of the formula (1) containing at least one part-structure M(L)$_n$ of the formula (2), identically or differently at each instance, characterized in that Y is a spiro carbon atom.

It is evident from the structures for the above-described inventive compounds of the formula (1) that the part-structure M(L)$_n$ of the formula (2) has a planar structure, the bridging group Y necessarily generating this planarity by virtue of the rigid bonding of the cycle 1 to the two fused part-cycles Cy2/Cy3 (or of the aryl to the isoquinoline ring). This property of the inventive compounds is in contrast to the nonplanarity of the systems of the formula A and B described in the literature to date. Here, either the hydrogen atoms on position 6 on the phenyl ring and 8 on the isoquinoline ring as in the compounds of the formula A or the bridge containing 2-20 alkyl bridge carbon atoms as in compounds of the formula B prevent the flattening of the bonded aryl part-ring systems. This fundamental structural difference of the above-mentioned substance classes from the inventive compounds has far-reaching consequences for the quantum efficiency of luminescence. In accordance with the generally observed trend in the optical spectroscopy of fused and condensed heteroaromatic systems (N. Turro, University Science Books, 55D Gate Five Road, Sausalito, Calif. 94965, ISBN 0-935702-71-7), the stiffer, planar systems here too have the greater luminescence quantum yields in comparison to the more flexible, nonplanar systems of the formula A and B. Greater luminescence quantum yields lead, as expected, in the OLED to distinctly improved efficiencies of the inventive compounds of the formula (1).

The present invention further provides the compounds of the formula (4)

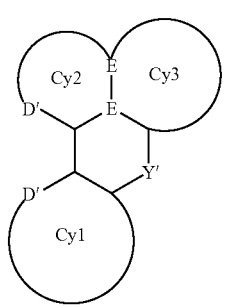

Formula (4)

where the symbols E, Cy1, Cy2 and Cy3 are each defined as described above, and the further symbols are:

Y' is the same or different at each instance and is BR$^1$, CR$_2$, C=NR$^1$, C=CR$_2$, SiR$^1{}_2$, PR$^1$, AsR$^1$, SbR$^1$, BiR$^1$, P(O)R$^1$, P(S)R$^1$, P(Se)R$^1$, As(O)R$^1$, As(S)R$^1$, As(Se)R$^1$, Sb(O)R$^1$, Sb(S)R$^1$, Sb(Se)R$^1$, Bi(O)R$^1$, Bi(S)R$^1$, Bi(Se)R$^1$, Se, SO, SeO, TeO, SO$_2$, SeO$_2$, TeO$_2$;

D' is the same or different at each instance and is C—H, N or P, with the proviso that one symbol D' is C—H and the other symbol D' is N or P.

Preference is given to compounds of the formula (4a)

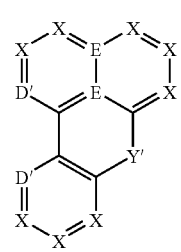

Formula (4a)

where the symbols are each defined as described above for formula (2a) and for formula (4).

A preferred embodiment of the present invention is that of the compounds of the formula (4b)

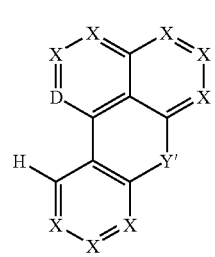

Formula (4b)

where D is N or P and the further symbols are each defined as described above for formula (2b) and (4a).

Preferred embodiments of the compounds of the formula (4) or (4a) or (4b) are analogous to the remarks made above for the part-structures of the formula (2) or (2a) or (2b).

These compounds constitute the ligands L to the above-mentioned compounds of the formula (1) and are thus useful intermediates for the synthesis of these compounds.

The inventive compounds of the formula (4) or (4a) or (4b) can be prepared by common organic chemistry processes, which will be described below by way of example:

1) 7,7-Difluorodibenzo[de,h]quinoline (see also Example 1)

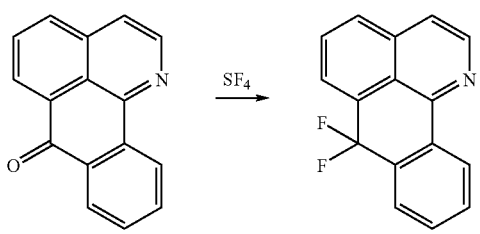

The direct fluorination of azobenzanthrone and analogous 7H-dibenzo[de,h]quinolin-7-ones with sulfur tetrafluoride, if appropriate in the presence of a Lewis acid, leads smoothly and in good yields to the 7,7-difluoro analogues.

2) 7,7-Dimethyldibenzo[de,h]isoquinoline (see also Example 2)

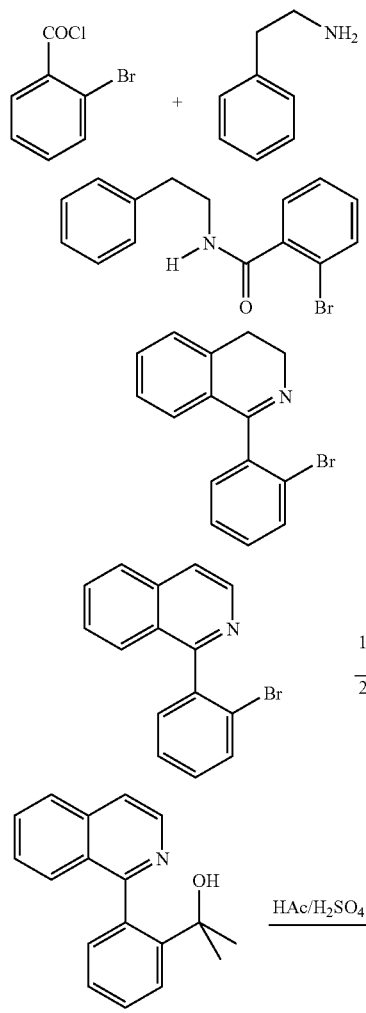

By the route shown above, symmetrically 7,7-disubstituted 7H-dibenzo[de,h]quinolines are obtainable in good yields. Analogously, replacement of acetone in step 4 by other ketones can readily afford further derivatives. For instance, the use of the ketone pentan-3-one leads to a ligand system as shown in example structure 3, that of benzophenone to a ligand system as shown in example structure 7. The use of cyclic ketones, for example of cyclopentanone or fluorenone, leads to the ligand systems as shown in example structures 6 and 8, i.e. to ligand systems with a spiro carbon atom. Alternatively, it is also possible, instead of the ketone, to use methyl chloroformate which is reacted in the subsequent step with an organolithium reagent or a Grignard compound. When, instead of the 2-bromo-benzoyl chloride, other functionalized 2-bromobenzoyl chlorides are used, it is possible to obtain 7,7-dialkyl-7H-dibenzo[de,h]isoquinolines functionalized on the phenyl ring. For instance, the use of 2-bromonicotinyl chloride, 2-bromoisonicotinyl chloride, 2-bromo-4-fluorobenzoyl chloride, 2-bromo-3,4-dimethylbenzoyl chloride, 2-bromo-3-methyl-4-fluorobenzoyl chloride, 2-bromo-3-cyano-4-fluorobenzoyl chloride leads to ligand systems as shown in example structures 13, 14, 16, 17, 18 and 19.

3) 7-Alkyl-/7-Aryl-7-alkoxydibenzo[de,h]quinolines

7-Alkyl-/7-Aryl-7-fluorodibenzo[de,h]quinolines

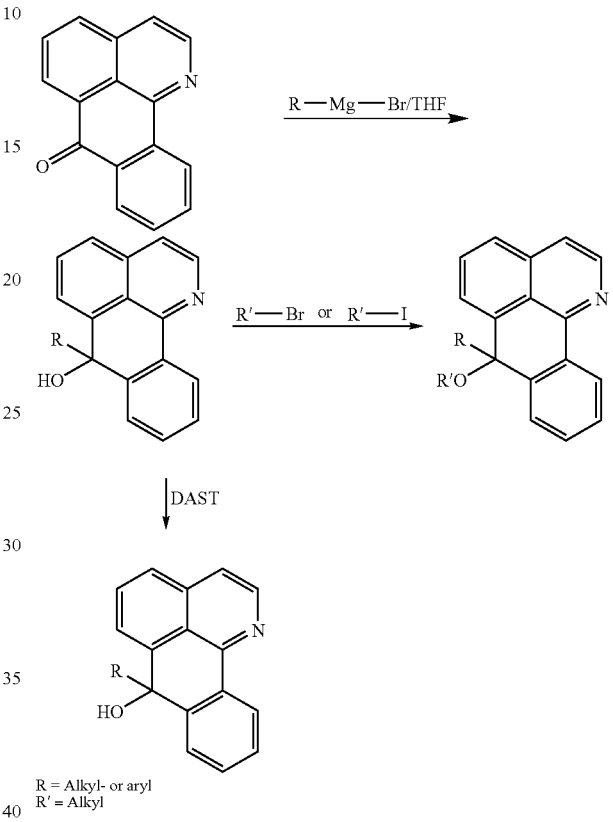

R = Alkyl- or aryl
R' = Alkyl

The compounds of the formula (4a) or (4b) substituted unsymmetrically in position 7 with alkyl or aryl and alkoxy or fluorine may, as shown above, be obtained by consecutive C-alkylation or C-arylation of the carbonyl function of azobenzanthrone with the aid of Grignard or organolithium reagents or other organometallic reagents and subsequent alkylation or fluorination (for example with DAST=diethylaminosulfur trifluoride) of the hydroxyl group. This reaction sequence leads to ligand systems including those shown in example structures 9, 10 and 12.

4) 7,7-Y'Dibenzo[de,h]quinolines

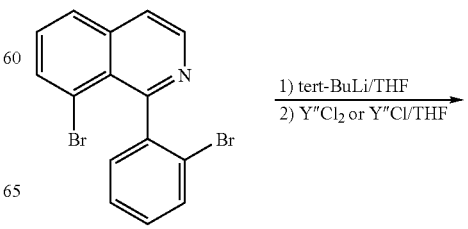

-continued

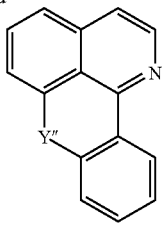

Y″ = BR¹, SiR₂¹, PR¹, AsR¹, SbR¹, BiR¹

When the 2-(3-bromophenyl)ethylamine is used instead of 2-phenylethylamine in the above-described synthesis sequence 2), the 1-(2-bromophenyl)-8-bromoisoquinoline is obtained entirely analogously and leads after double lithiation and subsequent reaction with the electrophiles Y″Cl₂ and Y″Cl to ligand systems as shown in the example structures 25, 26, 30 and 32.

If appropriate, these may, as shown in the cases of the example structures 30 and 32, be functionalized further by oxidation with air or hydrogen peroxide to give ligand systems as shown in example structures 31 and 33.

The inventive metal complexes can in principle be prepared by various processes; however, the process described below has been found to be particularly suitable.

The present invention therefore further provides a process for preparing the metal complexes by reacting the compounds of the formula (4), (4a) or (4b) with metal alkoxides of the formula (5), with metal ketoketonates of the formula (6) or mono- or polycyclic metal halides of the formula (7), (8) or (9)

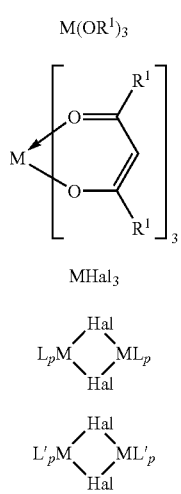

Formula (5)

M(OR¹)₃

Formula (6)

Formula (7)

MHal₃

Formula (8)

Formula (9)

where the symbols M and R¹ are each as defined above, p=1 or 2 and Hal=F, Cl, Br or I.

If appropriate, it is also possible with preference to use iridium compounds which bear both alkoxide and/or halide and/or hydroxyl radicals and ketoketonate radicals. These compounds may also be charged. Corresponding iridium compounds which are particularly suitable as reactants have been disclosed in DE 10314102.2.

The synthesis of the complexes is preferably carried out in such a way as described in WO 02/060910 and DE 10314102.2.

It is noticeable that the inventive metal complexes are formed distinctly more rapidly under otherwise identical reaction conditions than the metal complexes of the prior art. Therefore, the reaction time, deviating from the abovementioned prior art processes, is preferably in the range from 1 to 60 h, more preferably in the range from 20 to 50 h.

This process can afford the inventive compounds of the formula (1) in high purity, preferably more than 99% (determined by means of ¹H NMR and/or HPLC).

It is possible with the synthesis methods illustrated here to prepare compounds including the example structures 1 to 95 shown below for the compounds of the formula (1).

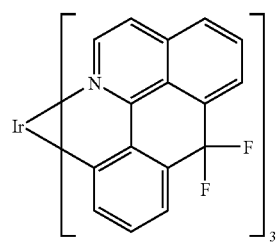

Example 1

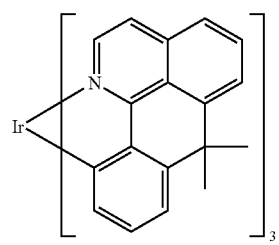

Example 2

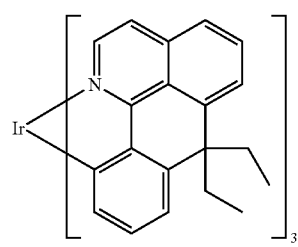

Example 3

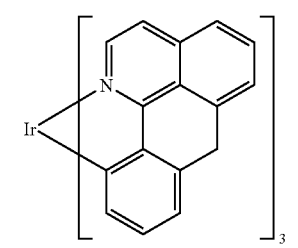

Example 4

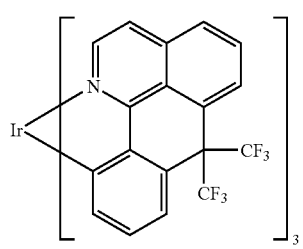

Example 5

Example 6

Example 7

Example 8

Example 9

Example 10

Example 11

Example 12

Example 13

Example 14

Example 15

Example 16

Example 17

Example 18
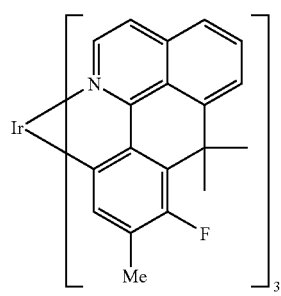
Example 19
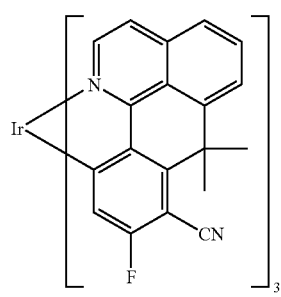
Example 20
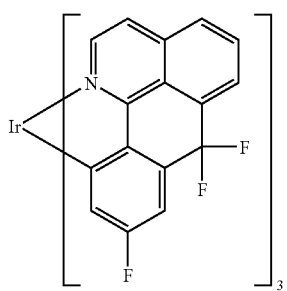
Example 21
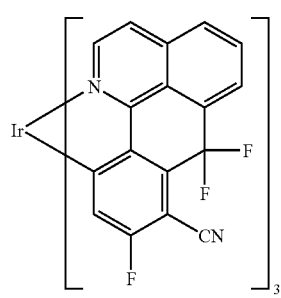
Example 22
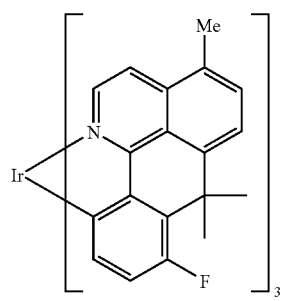
Example 23
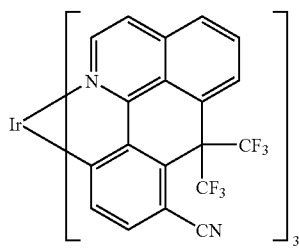
Example 24
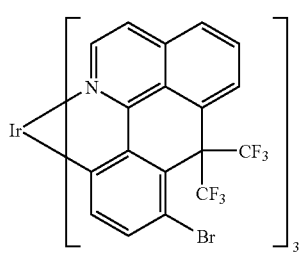
Example 25
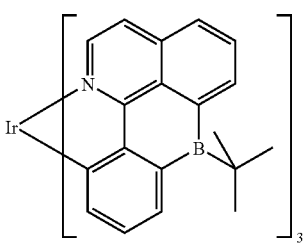
Example 26
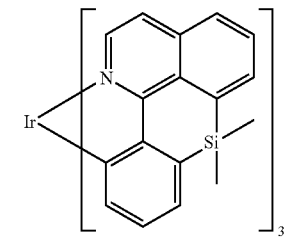
Example 27
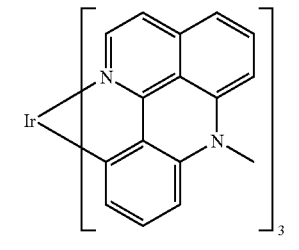
Example 28
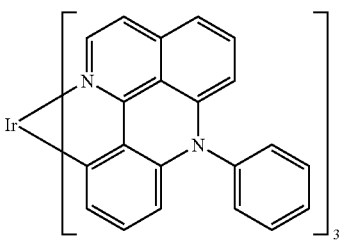

-continued
Example 29
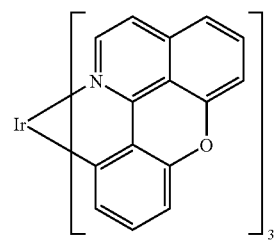
Example 30
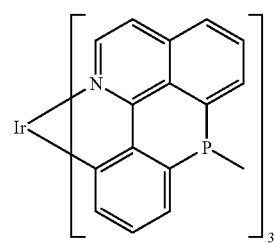
Example 31
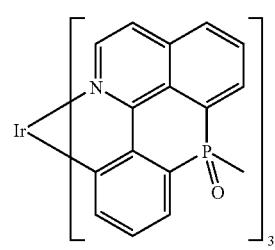
Example 32
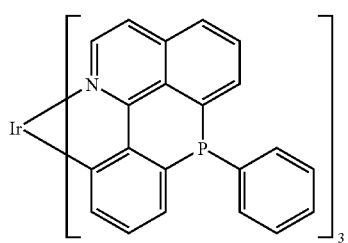
Example 33
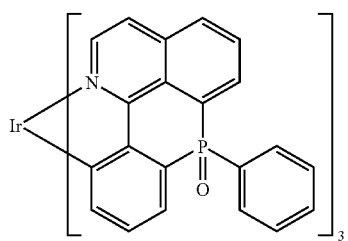
Example 34
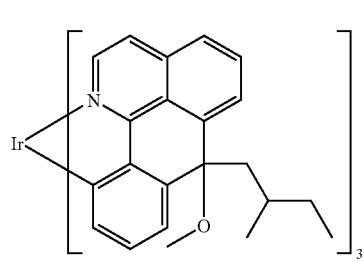
-continued
Example 35
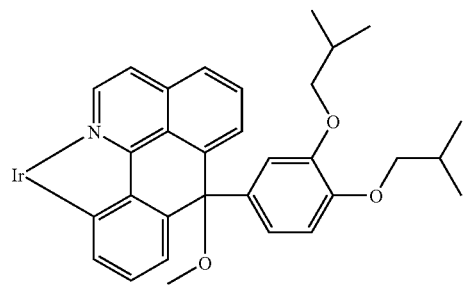
Example 36
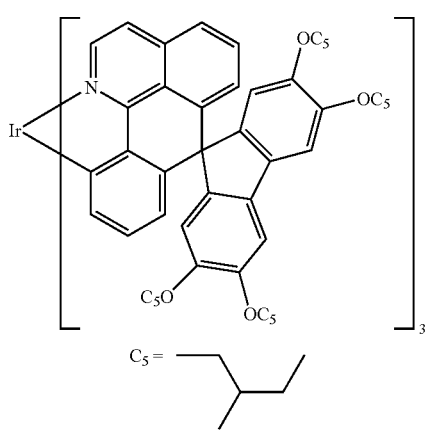
Example 37
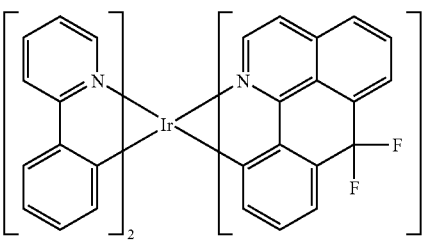
Example 37
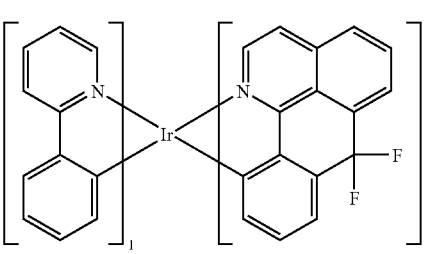
Example 39
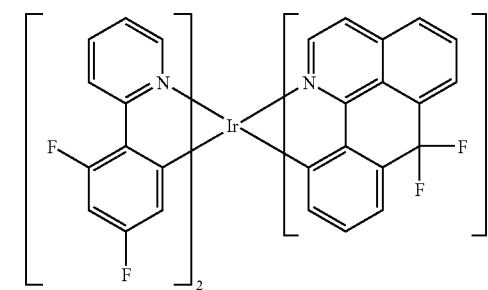

Example 40
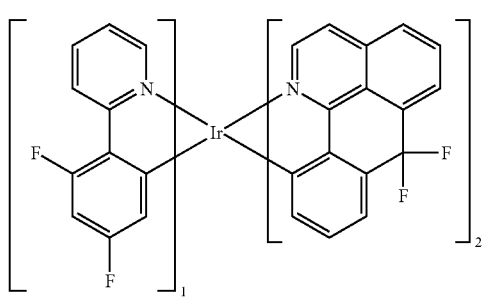
Example 41
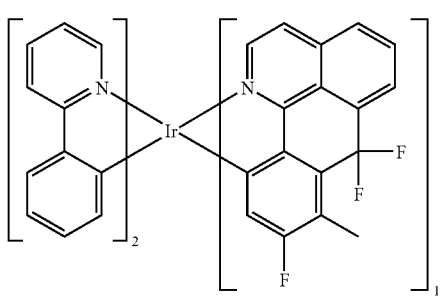
Example 42
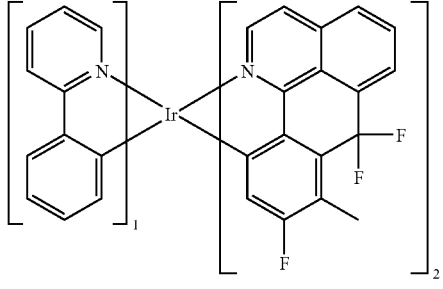
Example 43
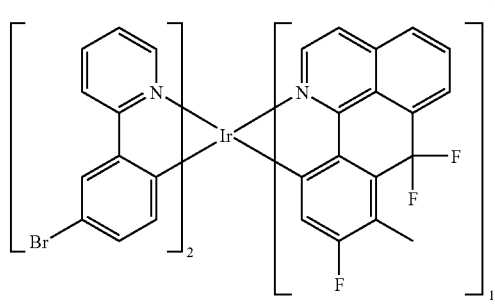
Example 44
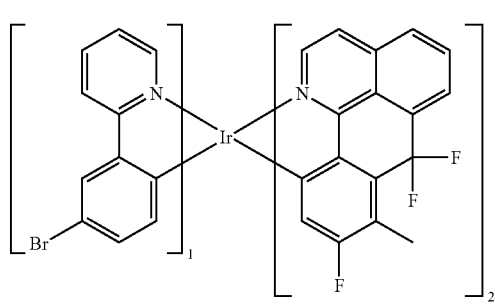
Example 45
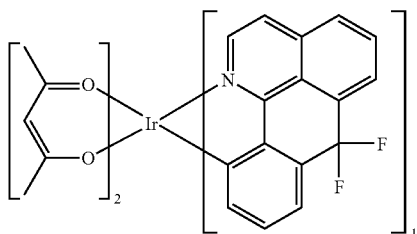
Example 46
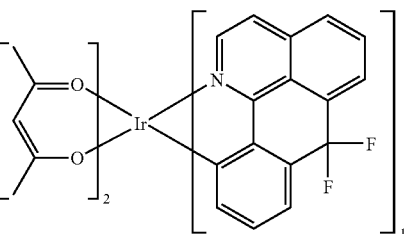
Example 47
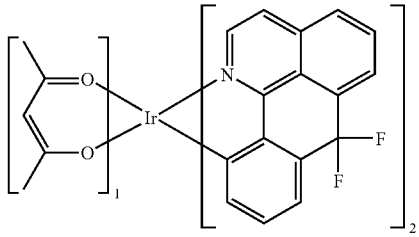
Example 48
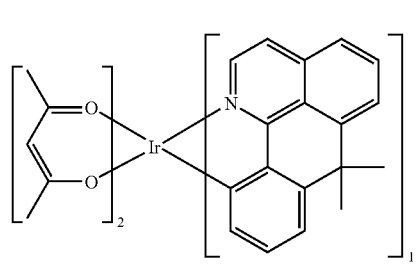
Example 49
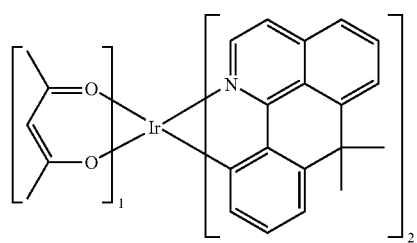
Example 50
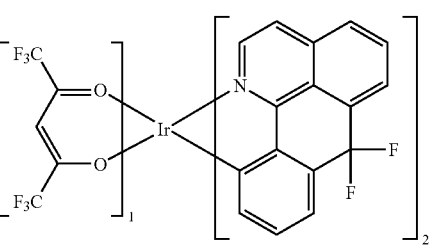

Example 51
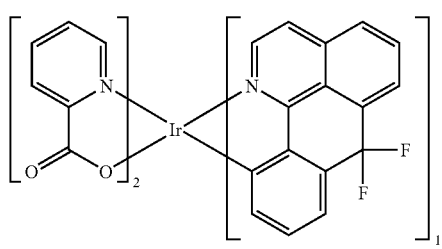
Example 52
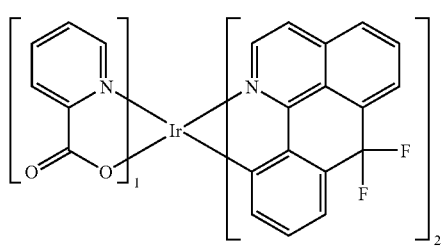
Example 53
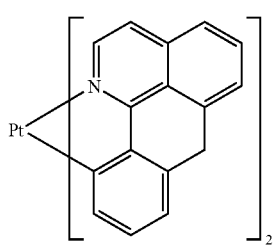
Example 54
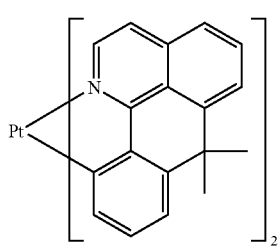
Example 55
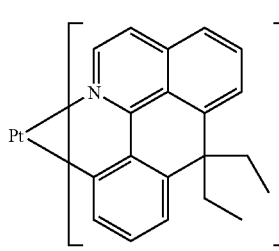
Example 56
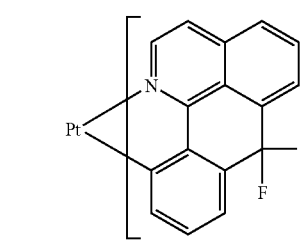
Example 57
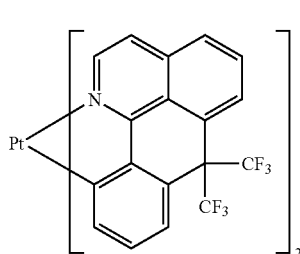
Example 58
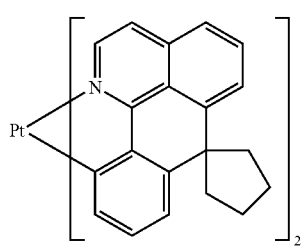
Example 59
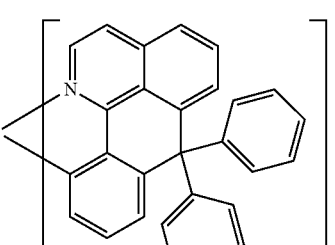
Example 60
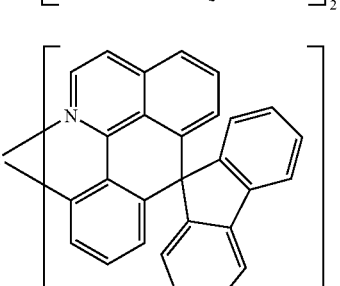
Example 61
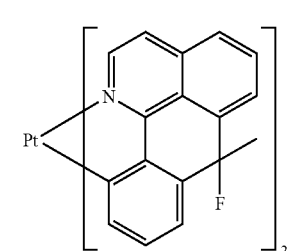
Example 62
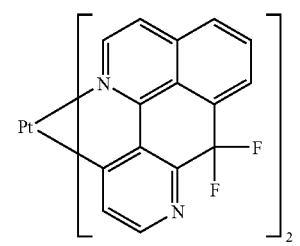

-continued
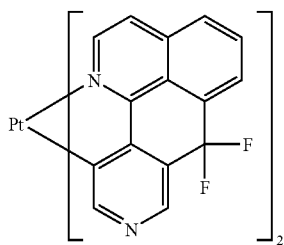
Example 63
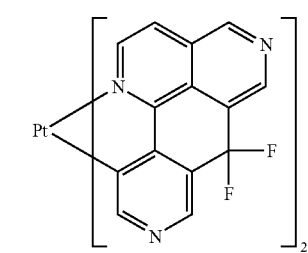
Example 64
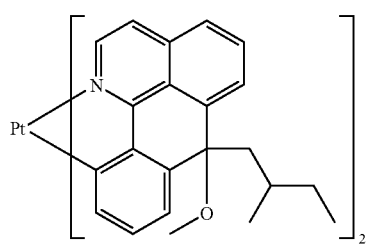
Example 65
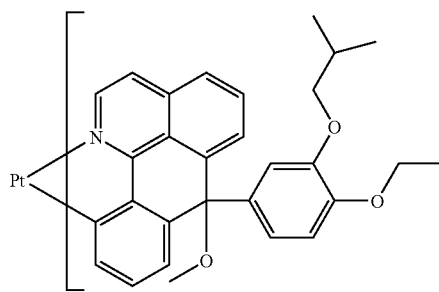
Example 66
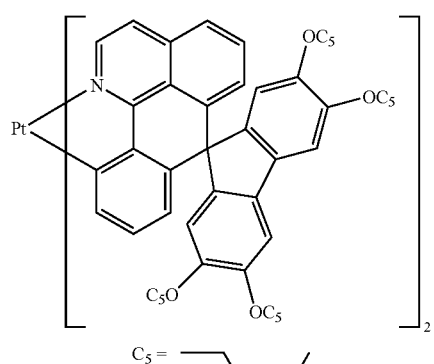
Example 67
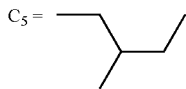
-continued
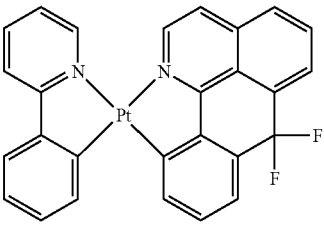
Example 68
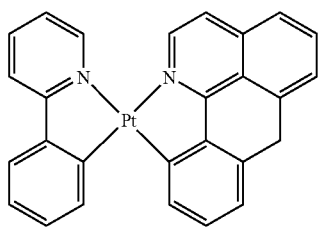
Example 69
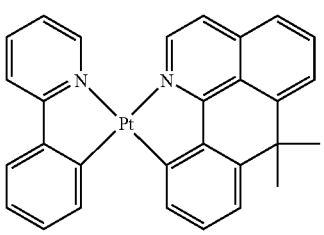
Example 70
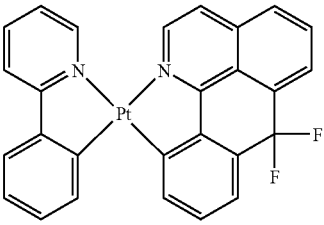
Example 71
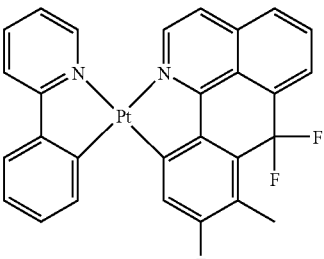
Example 72
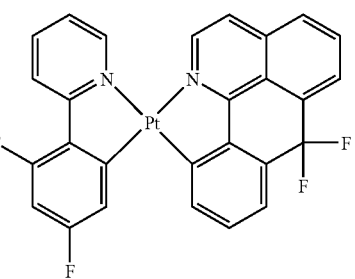
Example 73

-continued
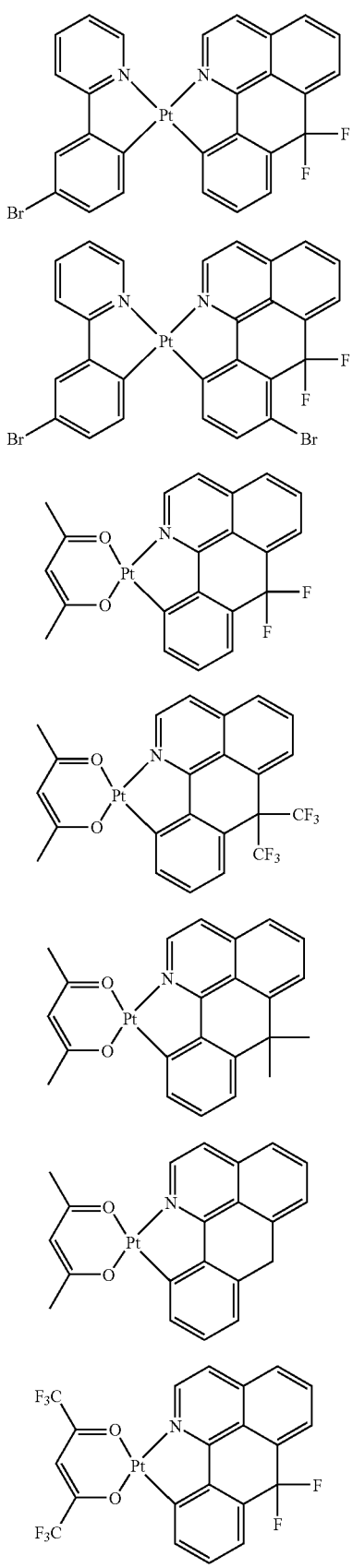
Example 74
Example 75
Example 76
Example 77
Example 78
Example 79
Example 80
-continued
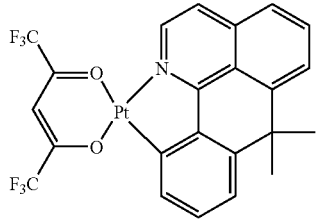
Example 81
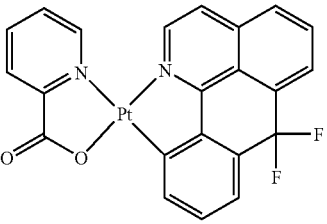
Example 82
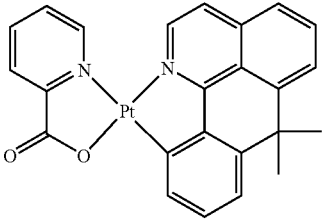
Example 83
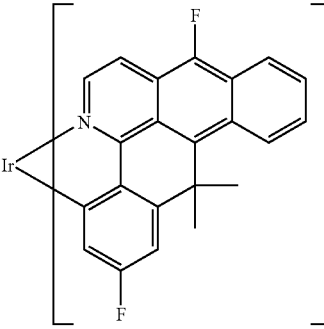
Example 84
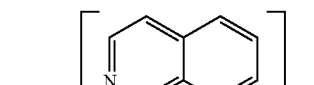
Example 85
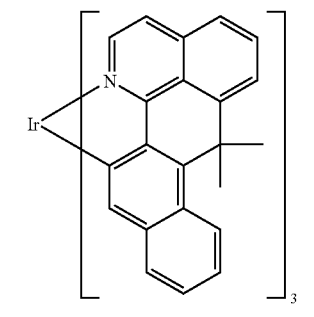
Example 86
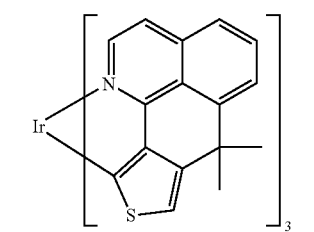

-continued

Example 87
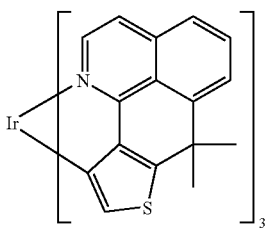

Example 88
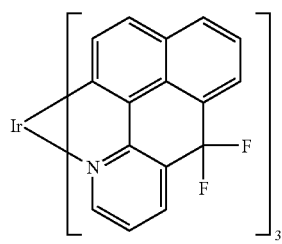

Example 89
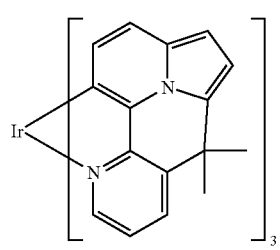

Example 90
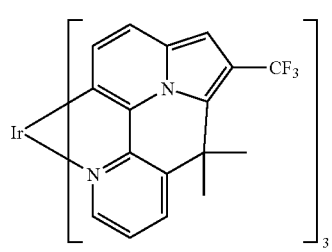

Example 91
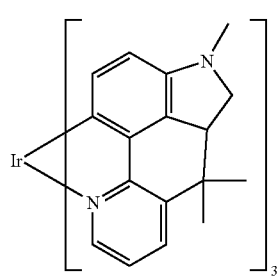

Example 92
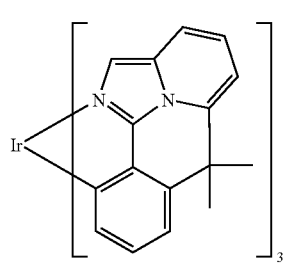

-continued

Example 93
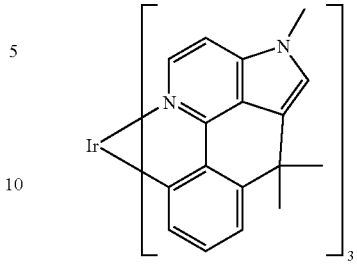

Example 94
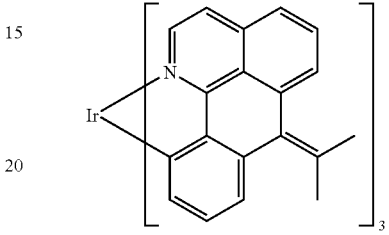

Example 95
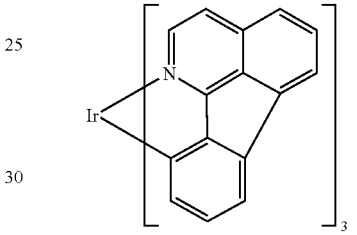

The above-described inventive compounds, for example compounds according to examples 24, 43, 44, 74 and 75, may also find use as comonomers and units for the formation of corresponding conjugated, part-conjugated or nonconjugated polymers or dendrimers. The appropriate polymerization into the main chain or into the side chains is effected preferably via the bromine functionality. For instance, they may be polymerized, inter alia, into soluble polyfluorenes (for example according to EP 842208 or WO 00/22026), polyspirobifluorenes (for example according to EP 707020 or EP 894107), polyparaphenylenes (for example according to WO 92/18552), polycarbazoles (for example according to DE 10304819.7 or DE 10328627.6) or else polythiophenes (for example according to EP 1028136), or else into copolymers which contain a plurality of different units among these.

The invention thus further provides conjugated, part-conjugated or nonconjugated polymers or dendrimers containing one or more compounds of the formula (1) where the above-defined R constitutes a bond to the polymer or dendrimer.

The abovementioned polymers, copolymers and dendrimers are notable for their good solubility in organic solvents.

Moreover, the inventive compounds of the formula (1) may of course also be functionalized further by common reaction types and thus converted to extended compounds of the formula (1). An example to be mentioned here is the functionalization with allylboronic acids according to SUZUKI or with amines according to HARTWIG-BUCHWALD.

The inventive compounds, polymers, dendrimers or extended compounds of the formula (1) find use as active components in electronic components, for example organic light-emitting diodes (OLEDs), organic integrated circuits (O-ICs), organic field-effect transistors (O-FETs), organic thin-film transistors (O-TFTs), organic solar cells (O-SCs) or else organic laser diodes (O-lasers).

The present invention thus further provides for the use of the inventive compounds of the formula (1), of the inventive polymers and dendrimers and of corresponding extended compounds of the formula (1) as an active component in electronic components.

The present invention further provides electronic components, especially organic light-emitting diodes (OLEDs), organic integrated circuits (O-ICs), organic field-effect transistors (O-FETs), organic thin-film transistors (O-TFTs), organic solar cells (O-SCs) or else organic laser diodes (O-lasers), comprising one or more inventive compounds of the formula (1), inventive polymers and dendrimers and corresponding extended compounds of the formula (1).

The present invention is illustrated in detail by the examples which follow without any intention that it be restricted thereto. The person skilled in the art can prepare further inventive compounds or apply the process according to the invention from the remarks without inventive activity.

EXAMPLES

The syntheses which follow were, unless stated otherwise, performed under a protective gas atmosphere in dried solvents. The reactants were purchased from ALDRICH [2-bromobenzoyl chloride, 3-fluoro-4-methylbenzeneboronic acid, manganese dioxide, magnesium] and from Fluka [sulfur tetrafluoride]. 1-Aza-benzanthrone(7H-dibenzo[de,h]quinolin-7-one) was prepared according to the "Deutschen Reichs Patentschrift Nr.: 614196" [German Empire patent no. 614196].

Example 1

Synthesis of fac-tris[7,7-difluoro-7H-dibenzo[de,h]quinoline-$C^2$,N]iridium(III) (Ir1)

A: 7,7-Difluorodibenzo[de,h]quinoline

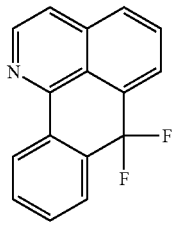

23.1 g (100 mmol) of 1-azabenzanthrone was initially charged in an inertized bomb tube. Subsequently, 22.7 g (210 mmol) of sulfur tetrafluoride were condensed in. This reaction mixture was heated to 180° C. for 10 h. After the bomb tube had been cooled and the excess sulfur tetrafluoride had been vented, the brown residue was recrystallized twice from dioxane/ethanol (4:1).

The yield at a purity of approx. 99.0% was 18.3 g (72.3 mmol), 72.3% of theory.

$^1$H NMR (CDCl$_3$): [ppm]=8.86 (m, 1H), 8.73 (m, 1H), 8.62 (m, 1H), 8.40 (m, 1H), 8.09 (m, 1H), 7.88 (m, 1H), 7.76 (m, 1H), 7.70 (m, 1H), 7.60 (m, 1H).

B: fac-Tris[7,7-difluorodibenzo[de,h]quinoline-$C^2$, N]iridium(III) (Ir1)

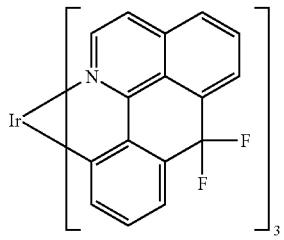

A mixture of 15.20 g (60 mmol) of 7,7-difluoro-7H-dibenzo[de,h]quinoline and 4.90 g (10 mmol) of iridium(III) acetylacetonate, suspended in 200 ml of ethylene glycol, was stirred at 165° C. for 140 h. After cooling to room temperature, a mixture of 160 ml of ethanol and 40 ml of 1N HCl was added dropwise. After stirring for 20 min, the deep red, finely crystalline precipitate was filtered off with suction, washed four times with 50 ml of a mixture of ethanol/1N HCl (4:1), four times with 50 ml of a mixture of ethanol/water (4:1) and four times with ethanol, and subsequently dried under reduced pressure. After high-vacuum sublimation (p=10$^{-5}$ mbar, T=385° C.), the yield at a purity of approx. 99.8% was 7.80 g (8.2 mmol), 82.2% of theory.

MS (FAB, m/z): M$^+$=949.7.

Example 2

Synthesis of fac-Tris[7,7-dimethyldibenzo[de,h] quinoline-$C^2$,N]iridium(III) (Ir2)

A: N-Phenylethyl-2-bromobenzamide

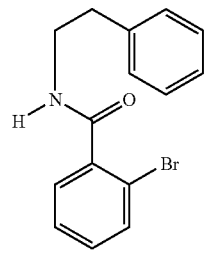

A mixture of 62.7 ml (500 mmol) of phenylethylamine, 70.4 ml (506 mmol) of triethylamine and 150 ml of dichloromethane was admixed dropwise at 0° C. with a solution of 109.2 g of 2-bromobenzoyl chloride in 50 ml of dichloromethane with good stirring at such a rate that the temperature did not exceed 30° C. Subsequently, the mixture was stirred at room temperature for a further 1 h. The colorless solid thus obtained was filtered off with suction, washed three times with 200 ml of dichloromethane and dried under reduced pressure. The yield at a purity of approx. 99.0% was 138.2 g (453 mmol), 90.7% of theory.

$^1$H NMR (CDCl$_3$): [ppm]=7.55 (m, 1H), 7.44 (m, 1H), 7.34-7.28 (m, 4H), 7.28-7.21 (m, 3H), 6.18 (br. t, NH, 1H), 3.73 (dt, NCH$_2$CH$_2$, 2H), 2.95 (t, NCH$_2$CH$_2$, 2H).

B: 1-(2-Bromophenyl)-3,4-dihydroisoquinoline

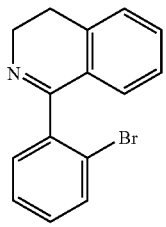

A suspension of 50.0 g (164 mmol) of N-phenylethyl-2-bromobenzamide and 27.9 g of phosphorus pentoxide in 200 ml of xylene was heated to 100° C. and admixed dropwise with 45.6 g (492 mmol) of phosphorus oxychloride. Subsequently, the reaction mixture was heated under reflux for 2 h. After cooling to 80° C., the reaction mixture was stirred into 4000 g of ice and adjusted to pH=12 with NaOH (solid). The organic phase was removed, the aqueous phase was extracted three times with 300 ml of toluene, and the combined organic phases were washed with 500 ml of water and subsequently dried over magnesium sulfate. After the desiccant had been filtered off and the solvent had been removed, the product was obtained as a yellow oil. The yield at a purity of approx. 99.0% was 46.9 g (164 mmol), 99.9% of theory.

$^1$H NMR (CDCl$_3$): [ppm]=7.61 (m, 1H), 7.41 (m, 2H), 7.38-7.34 (m, 1H), 7.30-7.24 (m, 2H), 7.19-7.16 (m, 1H), 6.89 (m, 1H), 4.10 (br. m, 1H), 3.73 (br. m, 1H), 2.88 (br. m, 2H).

C: 1-(2-Bromophenyl)isoquinoline

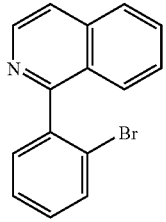

A mixture of 28.6 g (100 mmol) of 1-(2-bromophenyl)-3,4-dihydroisoquinoline, 86.9 g (1 mol) of manganese dioxide and 200 ml of 1,2-dichlorobenzene was stirred at 180° C. for 5 h. After cooling, the mixture was diluted with 500 ml of toluene and filtered through silica gel. After the solvent had been removed, the product was obtained as a yellow oil. The yield at a purity of approx. 99.0% was 26.0 g (91 mmol), 91.4% of theory.

$^1$H NMR (CDCl$_3$): [ppm]=8.63 (m, 1H), 7.86 (m, 1H), 7.73-7.61 (m, 4H), 7.51-7.42 (m, 3H), 7.37-7.33 (m, 1H).

D: 1-(2-(2-Hydroxy-iso-propyl)phenyl)isoquinoline

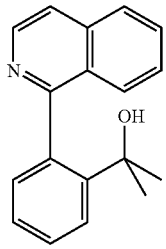

A Grignard compound prepared from 22.7 g (80 mmol) of 1-(2-bromo-phenyl)isoquinoline and 2.1 g (85 mmol) of magnesium in 200 ml of THF was admixed dropwise at 0° C. with a mixture of 8.8 ml (120 mmol) of acetone and 100 ml of THF. After warming to room temperature, the reaction mixture was heated under reflux for 3 h. After cooling, 800 ml of ethyl acetate and 500 ml of water were added, the organic phase was removed and the aqueous phase was extracted twice more with 200 ml of ethyl acetate. The combined organic phases were washed with saturated sodium chloride solution and dried over magnesium sulfate. After the solvent had been removed, the product was obtained as a yellow oil. The yield at a purity of approx. 99.0% was 19.2 g (73 mmol), 91.2% of theory.

$^1$H NMR (CDCl$_3$): [ppm]=8.66 (m, 1H), 7.74 (m, 1H), 7.70-759 (m, 4H), 7.50-7.43 (m, 3H), 7.34-7.30 (m, 1H), 4.87 (br. s, 1H, OH), 2.15 (s, 6H, CH$_3$).

E: 7,7-Dimethyldibenzo[de,h]quinoline

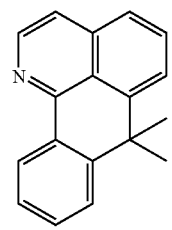

A solution of 13.2 g (50 mmol) of 1-(2-(2-hydroxy-isopropyl)phenyl)isoquinoline in 250 ml of acetic acid was admixed with 50 ml of conc. sulfuric acid and heated under reflux for 16 h. After cooling, the reaction mixture was poured onto 1000 g of ice, adjusted to pH=10 with 5N sodium hydroxide solution and extracted three times with 300 ml of dichloromethane. The combined organic phases were washed with water and dried over magnesium sulfate. After removal of the solvent and recrystallization from toluene/ethanol (5:1), the product was obtained as a yellow solid. The yield at a purity of approx. 99.0% was 8.4 g (34 mmol), 68.4% of theory.

$^1$H NMR (CDCl$_3$): [ppm]=8.41 (m, 1H), 7.94 (m, 1H), 7.77-769 (m, 3H), 7.61 (m, 1H), 7.45-7.40 (m, 3H), 7.27-7.21 (m, 1H), 2.65 (s, 6H, CH$_3$).

F: fac-Tris[7,7-dimethyldibenzo[de,h]quinoline-C$^2$,N]iridium(III) (Ir2)

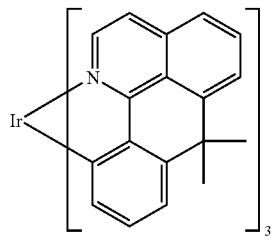

A mixture of 14.72 g (60 mmol) of 7,7-dimethyl-7H-dibenzo[de,h]quinoline and 4.90 g (10 mmol) of iridium(III) acetylacetonate, suspended in 200 ml of ethylene glycol, was stirred at 165° C. for 140 h. After cooling to room temperature, a mixture of 160 ml of ethanol and 40 ml of 1N HCl was added dropwise. After stirring for 20 min, the deep red, finely crystalline precipitate was filtered off with suction, washed four times with 50 ml of a mixture of ethanol/1N HCl (4:1), four times with 50 ml of a mixture of ethanol/water (4:1) and four times with ethanol, and subsequently dried under reduced pressure. After high-vacuum sublimation (p=10$^{-5}$ mbar, T=385° C.), the yield at a purity of approx. 99.8% was 7.97 g (8.6 mmol), 86.1% of theory.

MS (FAB, m/z): M$^+$=925.9.

$^1$H NMR (CD$_2$Cl$_2$): [ppm]=7.72 (d, J=7.96 Hz, 1H), 7.69 (t, J=8.03 Hz, 1H), 7.60 (d, J=8.03 Hz, 1H), 7.48 (d, J=6.36 Hz, 1H), 7.22 (d, J=6.36 Hz, 1H), 7.03 (d, J=6.36 Hz), 7.03 (d, J=7.70 Hz, 1H), 6.88 (t, J=7.7 Hz, 1H), 6.72 (d, J=7.37 Hz, 0.1H), 1.69 (s, 3H, CH$_3$), 1.71 (s, 3H, CH$_3$).

Example 3

Synthesis of fac-tris[7,7-dimethyldibenzo-13-fluoro[de,h]quinoline-C$^2$,N]iridium(III) (Ir3)

A: N-Phenylethyl-3-fluorobenzamide

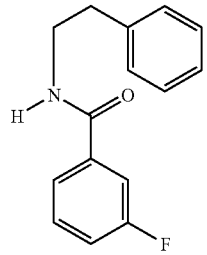

174.9 ml (1.39 mol) of phenylethylamine were dissolved in 600 ml of dichloromethane and admixed with 196.0 ml (1.41 mol, 1.01 eq.) of triethylamine. Subsequently, 221.0 g (1.39 mmol) of 3-fluorobenzoyl chloride were added dropwise to the solution at 0° C. such that the temperature did not rise above 40° C. The mixture was stirred at RT for 18 h and the precipitated solid was dissolved in 1000 ml of dichloromethane. The mixture was washed four times with 200 ml of dilute NaOH, 1N HCl and saturated NaHCO$_3$ solution. The organic phase was removed, dried over MgSO$_4$ and concentrated under reduced pressure. The solid was filtered off with suction and washed twice with a little dichloromethane. 289.52 g of a white solid were obtained with >99% purity (by HPLC), corresponding to 85.4% of theory.

$^1$H NMR (CDCl$_3$): [ppm]=7.42 (dd, J=7.03 Hz, 1.67 Hz, 1H), 7.3-7.39 (m, 3H), 7.24 (m$_c$, 3H), 7.17 (dt, J=9.03 Hz, 1.68 Hz, 1H), 6.1 (s$_{br}$, 1H, NH), 3.70 (t, J=7.02 Hz, 2H, CH$_2$), 2.90 (t, J=7.03 Hz, 2H, CH$_2$).

B: 1-(3-Fluorophenyl)-3,4-dihydroisoquinoline

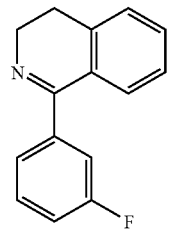

289.0 g (1.19 mol) of N-phenylethyl-3-fluorobenzamide were dissolved in 1000 ml of xylene and admixed at 90° C. in portions with 202.7 g (1.43 mol, 1.2 eq.) of phosphorus pentoxide. Subsequently, 326.8 ml (3.57 mol, 3.0 eq.) of phosphorus oxychloride were added dropwise. The mixture was heated under reflux for 4 h. The reaction solution was subsequently poured while hot onto ice and adjusted cautiously to pH=12 with solid NaOH with ice cooling. The precipitate was extracted three times with 500 ml of toluene, dried over MgSO$_4$ and concentrated under reduced pressure to a highly viscous oil which later crystallizes. 267.41 g are obtained with a purity of approx. 99%, corresponding to 99.8% of theory.

$^1$H NMR (CDCl$_3$): [ppm]=7.37 (m$_c$, 3H), 7.33 (dd, J=9.3, 2.0 Hz, 1H), 7.26 (d, J=7.8 Hz, 1H), 7.24 (d, J=3.68 Hz, 2H), 7.12 (m$_c$, 1H), 3.84 (t, J=7.36 Hz, 2H, CH$_2$), 2.79 (t, J=7.36 Hz, 2H, CH$_2$).

C: 1-(3-Fluorophenyl)isoquinoline

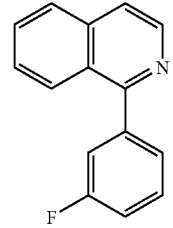

266.41 g (1.183 mol) of 1-(3-fluorophenyl)-3,4-dihydroisoquinoline were dissolved in 1500 ml of o-dichlorobenzene and admixed with 901.2 g (10.37 mol, 8.7 eq.) of manganese. The mixture was stirred at 160-170° C. for 16 h. Subsequently, the reaction solution was filtered through Celite which was rinsed with dichloromethane/ethanol (25:1). Subsequently, the solvent was distilled off under reduced pressure. 264.74 g of a crystalline solid with 99% purity were obtained, corresponding to 99% of theory.

$^1$H NMR (CDCl$_3$): [ppm]=8.59 (d, J=5.69 Hz, 1H), 8.05 (d, J=8.36 Hz, 1H), 7.83 (d, J=8.37 Hz, 1H), 7.65 (t, J=8.03 Hz, 1H), 7.12 (d, J=5.62 Hz, 1H), 7.46 (m$_c$, 2H), 7.42 (d, J=8.7 Hz, 1H), 7.17 (m$_c$, 1H).

D: 1-[3-Fluoro-2-(carboxymethyl)phenyl]isoquinoline

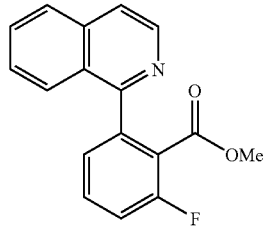

50.0 g (0.224 mol) of 1-(3-fluorophenyl)isoquinoline were dissolved in 1000 ml of THF and admixed dropwise at −78° C. with 134.4 ml (0.336 mol, 1.50 eq.) of n-butyllithium (2.5 M in hexane). After the addition had ended, the mixture was stirred at −78° C. for a further 3 h and the red-brown lithium organyl was subsequently transferred via a tube at −78° C. to a solution of 190.8 ml (2.47 mol, 11.0 eq.) of methyl chloroformate in 2000 ml of THF. The mixture was stirred at −78° C. up to −20° C. for a further 18 h. The reaction solution was quenched with EtOH with external ice cooling and concentrated to a third of the volume. Subsequently, the reaction solution was admixed with 300 ml of dichloromethane and washed three times each with 100 ml of NH$_4$Cl solution and NaHCO$_3$ solution and water, dried over MgSO$_4$ and concentrated under reduced pressure. The resulting highly viscous oil was crystallized from heptane. 44.68 g of a crystalline solid were obtained, corresponding to 70.4% of theory, with a purity of 98%.

$^1$H NMR (CDCl$_3$): [ppm]=8.56 (d, J=5.69 Hz, 1H), 7.89 (d, J=8.36 Hz, 1H), 7.86 (d, J=8.37 Hz, 1H), 7.69 (t, J=8.03 Hz, 1H), 7.66 (d, J=5.69 Hz, 1H), 7.55 (m$_c$, 2H), 7.37 (d, J=7.7 Hz, 1H), 7.27 (t, J=9.37 Hz, 1H), 3.46 (s, 3H, OMe).

E: 1-[2-(1-Methyl-1-hydroxyethyl)-3-fluorophenyl]
isoquinoline

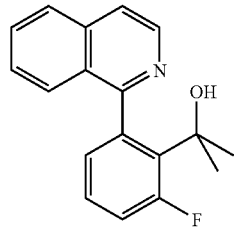

45.27 g (0.161 mol) of 1-[3-fluoro-2-(carboxymethyl)phenyl]isoquinoline were dissolved in 950 ml of THF and admixed dropwise at −78° C. with 185.12 ml (0.370 mol, 2.3 eq.) of methyllithium (2 M in diethyl ether). After the addition, the mixture was stirred at from −78° C. to −20° C. for 18 h. The reaction mixture was subsequently quenched with MeOH with ice cooling and admixed with 500 ml of dichloromethane. The mixture was subsequently washed three times with 100 ml of NaHCO$_3$ solution and water, dried over MgSO$_4$ and concentrated under reduced pressure. The resulting solid was crystallized from 600 ml of heptane. 29.72 g of a white solid were obtained, corresponding to 65.8% of theory, with a purity of 97.5%.

$^1$H NMR (DMSO-d6): [ppm]=8.42 (d, J=5.5 Hz, 1H), 7.84 (d, J=8.25 Hz, 1H), 7.65 (t, J=7.79 Hz), 7.62 (d (overlapping), J=6.24 Hz, 1H), 7.60 (d (overlapping), J=9.62 Hz, 1H), 7.48 (t, J=7.33 Hz, 1H), 7.27 (m$_c$, 1H), 7.17 (dd, J=12.38 Hz, 7.79 Hz), 6.96 (d, J=7.79 Hz), 1.90 (s$_{br.}$, 1H, OH), 1.67 (s, 3H, CH$_3$), 1.48 (s, 3H, CH$_3$).

F: 7,7-Dimethyl-8-fluorodibenzo[de,h]quinoline

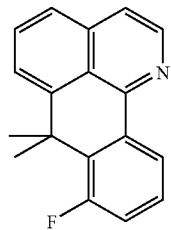

26.1 g (92.82 mmol) of 1-[2-(1-methyl-1-hydroxyethyl)-3-fluorophenyl]isoquinoline were added to a mixture at 150° C. of 260 ml of o-dichlorobenzene and 104.2 ml of H$_2$SO$_4$, and stirred for 60 min. The reaction solution was subsequently poured onto 1000 ml of ice and adjusted cautiously to pH=12 with solid NaOH with ice cooling. Subsequently, the mixture was extracted with 500 ml of dichloromethane, dried over MgSO$_4$ and concentrated under reduced pressure. The crude product was dissolved in 100 ml of toluene and air was introduced at 50° C. for 4 h. Subsequently, purification was effected by column chromatography with dichloromethane. 18.45 g of a solid were obtained, corresponding to 75.5% of theory, with a purity of 99.6%.

$^1$H NMR (CDCl$_3$): [ppm]=8.74 (d, J=8.03 Hz, 1H), 8.56 (d, J=5.69 Hz, 1H), 7.66-7.77 (m, 3H), 7.57 (d; J=5.69 Hz, 1H), 7.4 (m$_c$, 1H), 7.16 (dd, J=12.71 Hz, 8.03 Hz), 1.86 (s, 6H, CH$_3$).

G: fac-Tris[7,7-dimethyl-8-fluorodibenzo[de,h]
quinoline-C$^2$,N]iridium(III) (Ir3)

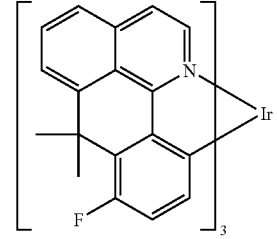

15.13 g (57.48 mmol, 5.93 eq.) of 7,7-dimethyl-13-fluorodibenzo[de,h]quinoline and 4.69 g (9.68 mmol) of Na[Ir(acac)$_2$Cl$_2$] were dissolved in 180 ml of degassed ethylene glycol (Spectranal) and stirred at 198° C. under an argon atmosphere for 48 h. The reaction solution was subsequently cooled to 50° C., added to 350 ml of a degassed mixture at 50° C. of EtOH/1N HCl, and stirred with exclusion of air for 60 min. The solid was filtered off with suction with the exclusion of air, washed with a mixture, degassed in each case, of EtOH/1N HCl (350 ml), EtOH/water (1:1, 350 ml) and EtOH (350 ml), and dried under reduced pressure. 8.45 g of a red solid were obtained and were recrystallized from toluene/ethanol (16:1). 5.29 g of a red powder were obtained, corresponding to 56.4% of theory, with a purity of 99.5%.

$^1$H NMR (CDCl$_3$): [ppm]=7.96 (d, J=7.69 Hz, 1H), 7.88 (t, J=7.7 Hz, 1H), 7.82 (d, J=7.7 Hz, 1H), 7.57 (d, J=6.36 Hz, 1H), 7.43 (d, J=6.36 Hz, 1H), 6.76 (dd, J=14.05 Hz, 8.03 Hz, 1H), 6.57 (dd, J=8.04 Hz, 5.36 Hz, 1H), 1.80 (s, 3H), 1.77 (s, 3H).

Example 4

Synthesis of fac-tris[7,7-dimethyl-8-fluoro-4-methyldibenzo[de,h]quinoline-$C^2$,N]iridium(III)

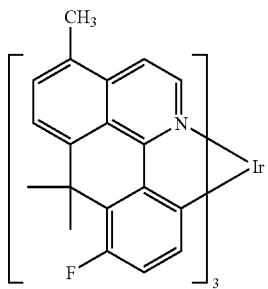

The synthesis of the compound Ir4 was performed analogously to the working methods 3A to 3G and was obtained with comparable yields and purities.

$^1$H NMR (pyridine-d5): [ppm]=7.68 (d, J=7.7 Hz, 1H), 7.58 (d, J=6.69 Hz, 1H), 7.50 (d, J=7.69 Hz, 1H), 7.39 (dd, J=8.37 Hz, 5.96 Hz, 1H), 7.12 (d, J=6.36 Hz, 1H), 6.97 (dd, J=13.72 Hz, 8.36 Hz, 1H), 2.38 (s, 3H, CH$_3$), 1.95 (s, 3H, CH$_3$), 1.90 (s, 3H, CH$_3$).

Example 5 fac-Tris[7,7-dimethyl-8-fluoro-4-methyldibenzo[de,h]quinoline-$C^2$,N]iridium(III) (Ir5)

A: 1-(3-Fluoro-4-methylphenyl)isoquinoline

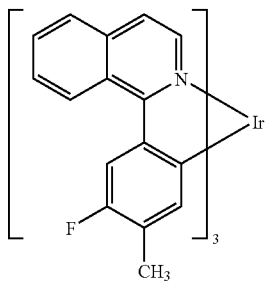

500 ml of degassed dioxane were initially charged and admixed with 10.0 g (61.14 mmol) of 1-chloroisoquinoline, 18.8 g (122.0 mmol, 2.0 eq.) of 3-fluoro-4-methylbenzeneboronic acid and 24.0 g (73.66 mmol, 1.2 eq.) of Cs$_2$CO$_3$. The reaction mixture was degassed for 10 min and admixed with 1.25 ml (5.49 mmol, 9 mol %) of t-Bu$_3$P and 0.412 g (1.83 mmol, 3 mol %) of Pd(OAc)$_2$. The mixture was stirred at 105° C. for 18 h, subsequently admixed with 400 ml of dichloromethane and washed three times with 200 ml of NaHCO$_3$ solution and water. Subsequently, the mixture was filtered through Celite, dried over MgSO$_4$ and concentrated under reduced pressure. The viscous oil was columned on silica gel with ethyl acetate/heptane (1:5). 10.47 g were obtained, corresponding to 72.2% of theory, with a purity of 99.5%.

$^1$H NMR (CDCl$_3$): [ppm]=8.60 (d, J=5.69 Hz, 1H), 8.12 (d, J=8.70 Hz, 1H), 7.89 (d, J=8.37 Hz, 1H), 7.70 (t, J=8.03 Hz, 1H) 7.65 (d, J=5.69 Hz, 1H), 7.55 (t, J=8.36 Hz, 1H), 7.39-7.35 (m, 2H), 7.34 (t, J=8.03 Hz, 1H), 2.40 (s, 3H, CH$_3$).

B: fac-Tris[7,7-dimethyl-8-fluoro-4-methyldibenzo[de,h]quinoline-$C^2$,N]iridium(III) (Ir5)

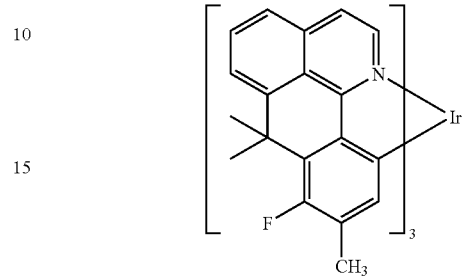

The further synthesis of Ir5 was effected analogously to the methods 3D to 3G. The products were obtained with comparable yields and purities.

$^1$H NMR (DMSO-d6): [ppm]=7.73 (d, J=4.86 Hz, 2H), 7.62 (t, J=4.69 Hz, 1H), 7.40 (d, J=6.36 Hz, 1H), 7.19 (d, J=6.36 Hz, 1H), 6.52 (d, J=7.69 Hz, 1H), 2.11 (s, 3H, CH$_3$), 1.89 (s, 3H, CH$_3$), 1.81 (s, 3H, CH$_3$).

Example 6

Comparison of the Thermal Stability with Ir(piq)$_3$

Ir(piq)$_3$ was synthesized according to US 2003/0068526. 2 g of the crude product described there were sublimed under high vacuum (p=10$^{-7}$ mbar, T=385° C.) to obtain 607 mg of an iridium-containing ash in addition to 1.38 g of sublimate corresponding to Ir(piq)$_3$ with a purity of 99.7% by HPLC. This thus shows that, in the sublimation at the same temperature as the inventive compounds, about a third of the product decomposes, while the inventive compounds can be sublimed virtually without loss, as can be taken from examples 1 and 2.

Example 7

Production and Characterization of Organic Electroluminescence Devices which Comprise Inventive Compounds Ir1

Inventive electroluminescence devices can be prepared as described, for example, in the patent application DE10330761.3.

Here, the results of two different OLEDs are compared. The fundamental structure, the materials used, degree of doping and their layer thicknesses was identical for better comparability. Only the dopant in the emission layer was varied.

The first example describes a comparative standard according to the prior art, in which the emitter layer consists of the host material CBP and the guest material Ir(piq)$_3$. In addition, an OLED with an emitter layer consisting of the host material CBP and the guest material fac-tris[7,7-difluorodibenzo[de,h]quinoline-$C^2$,N]iridium(III) (Ir1, synthesized according to example 1) is described. Analogously to the abovementioned general process, OLEDs with the following structure were obtained:

| | |
|---|---|
| PEDOT | 60 nm (spin-coated from water; PEDOT purchased from H. C. Starck, Goslar; poly-[3,4-ethylenedioxy-2,5-thiophene]), (HIL) |
| NaphDATA | 20 nm (applied by vapor deposition; NaphDATA purchased from SynTec; 4,4',4''-tris(N-1-naphthyl)-N-phenylamino)triphenylamine), (HTL) |
| S-TAD | 20 nm (applied by vapor deposition; S-TAD synthesized according to WO 99/12888; 2,2',7,7'-tetrakis(diphenylamino)spirobifluorene), (HTL) |
| Emitter layer: | (EML) |
| CPB | 20 nm (applied by vapor deposition; CPB purchased from ALDRICH and purified further, finally sublimed twice more; 4,4'-bis-(N-carbazolyl)biphenyl) |
| Ir1 | (20% doping, applied by vapor deposition; synthesized according to example 1) |
| OR: | |
| Ir(piq)$_3$ | (20% doping, applied by vapor deposition; synthesized according to example 6) |
| BCP | 10 nm (applied by vapor deposition; BCP purchased from ABCR, used as obtained; 2,9-dimethyl-4,7-diphenyl-1,10-phenanthroline), (HBL) |
| AlQ$_3$ | 10 nm (applied by vapor deposition: AlQ$_3$ purchased from SynTec; tris(quinolinato)aluminum(III)), (ETL) |
| Ba—Al | 3 nm of Ba, 150 nm of Al thereon. |

These OLEDs which were yet to be optimized were characterized in a standard manner; for this purpose, the electroluminescence spectra, the efficiency (measured in cd/A) as a function of the brightness, calculated from current-voltage-brightness characteristics (IUL characteristics), and the lifetime were determined.

Electroluminescence Spectra:

The OLEDs, both the comparative example with Ir(piq)$_3$ and the OLEDs with Ir1 as a dopant exhibit red emission with comparable color coordinates.

Efficiency as a Function of Brightness:

OLEDs produced with the dopant Ir(piq)$_3$ afford, under the conditions described above, typically a maximum efficiency of about 6.5 cd/A, and 6.2 V are required for the reference luminance of 100 cd/m$^2$. In contrast, OLEDs produced with the inventive dopant Ir1 exhibit a maximum efficiency of 8.7 cd/A, the required voltage for the reference luminance of 100 cd/m$^2$ even falling to 5.4 V.

Lifetime Comparison:

The two lifetime curves (FIG. 1) were shown in the same figure for better comparability. The figure shows the course of the brightness measured in cd/m$^2$ with time. The measurement was effected at constant current density of 10 mA/cm$^2$ at a temperature of 80° C., which corresponds to an accelerated measurement. The lifetime refers to the time after which 50% of the starting luminance is attained. At the brightnesses shown, a lifetime of approx. 130 h at a starting brightness of approx. 650 cd/m$^2$ is obtained for the dopant Ir(piq)$_3$. For the dopant Ir1, a starting brightness of approx. 900 cd/m$^2$ and a lifetime greater than 5000 h at 80° C. are obtained as the same current density, which corresponds to an increase in the lifetime by a factor of almost 40 compared to the OLEDs with Ir(piq)$_3$ as the dopant.

Examples 8 to 11

Further Device Examples with Inventive Dopants

The further inventive dopants Ir2 to Ir5 were also tested in OLEDs and compared with Ir(piq)$_3$ according to the prior art (example 8). Analogously to the process detailed in example 7, OLEDs were obtained with the following structure:

| | |
|---|---|
| PEDOT | 60 nm (spin-coated from water; PEDOT purchased from H. C. Starck, Goslar; poly-[3,4-ethylenedioxy-2,5-thiophene]), (HIL) |
| NaphDATA | 20 nm (applied by vapor deposition; NaphDATA purchased from SynTec; 4,4',4''-tris(N-1-naphthyl)-N-phenylamino)triphenylamine), (HTL) |
| S-TAD | 20 nm (applied by vapor deposition; S-TAD synthesized according to WO 99/12888; 2,2',7,7'-tetrakis(diphenylamino)spirobifluorene), (HTL) |
| Emitter layer: | (EML) |
| M1 | Bis(9,9'-spirobifluoren-2-yl) ketone (applied by vapor deposition, synthesized according to DE 10317556.3) |
| Ir2 to Ir5 | (applied by vapor deposition; synthesized according to example 2 to 5) |
| OR: | |
| Ir(piq)$_3$ | (applied by vapor deposition; synthesized according to example 6) |
| HBM1 | 2,7-Bis(4-biphenyl-1-yl)-2',7'-di-tert-butyl-spiro-9,9'-bifluorene (applied by vapor deposition; synthesized according to DE 10357317.8), (HBL); not used in all examples |

| | -continued |
|---|---|
| AlQ₃ | (applied by vapor deposition: AlQ₃ purchased from SynTec; tris(quinolinato)aluminum(III)), (ETL); not used in all examples |
| Ba—Al | 3 nm of Ba, 150 nm of Al thereon. |

The layer thicknesses were selected such that the total layer thickness of the emission layer, of the hole blocking layer and of the electron transport layer always added up to a total of 60 nm. The results which were obtained with these OLEDs are compiled in table 1. The matrix material M1, the hole blocking material HBM1 and the comparative dopant Ir(piq)₃ are depicted below for the sake of clarity:

TABLE 1

Device results with inventive dopants

| Experiment | EML | HBL | ETL | Max. efficiency [cd/A] | Max. power efficiency [lm/W] | Voltage [V] at 100 cd/m² | CIE (x, y) | Lifetime [h] at 10 mA/cm² |
|---|---|---|---|---|---|---|---|---|
| Example 8a (Comparative) | M1: 10% Ir(piq)₃ (30 nm) | HBM1 (10 nm) | AlQ₃ (20 nm) | 7.4 | 5.3 | 5.8 | 0.68/0.32 | 10200 |
| Example 8b (Comparative) | M1: 10% Ir(piq)₃ (60 nm) | — | — | 7.1 | 6.9 | 3.9 | 0.68/0.32 | 7400 |
| Example 9a | M1: 10% Ir3 (30 nm) | HBM1 (10 nm) | AlQ₃ (20 nm) | 10.3 | 7.5 | 5.7 | 0.66/0.34 | 12700 |
| Example 9b | M1: 10% Ir3 (40 nm) | — | AlQ₃ (20 nm) | 11.8 | 7.9 | 5.2 | 0.66/0.34 | 11900 |
| Example 9c | M1: 10% Ir3 (60 nm) | — | — | 14.9 | 11.0 | 4.0 | 0.66/0.34 | 9400 |
| Example 10a | M1: 10% Ir2 (30 nm) | HBM1 (10 nm) | AlQ₃ (20 nm) | 13.4 | 8.9 | 5.5 | 0.64/0.36 | 12200 |
| Example 11a | M1: 10% Ir5 (30 nm) | HBM1 (10 nm) | AlQ₃ (20 nm) | 12.4 | 6.7 | 5.9 | 0.65/0.35 | 11600 |
| Example 11b | M1: 10% Ir5 (60 nm) | — | — | 13.4 | 7.9 | 4.2 | 0.65/0.35 | 9800 |

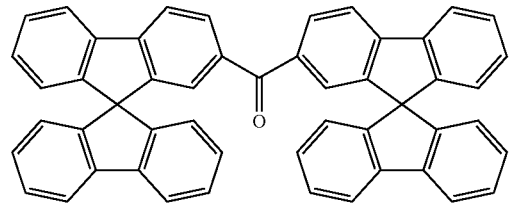

Bis(9,9'-spirobifluoren-2-yl) ketone
Matrix material M1

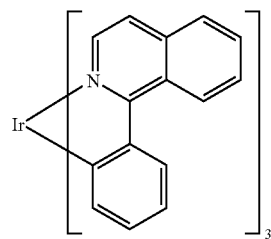

Ir(piq)₃

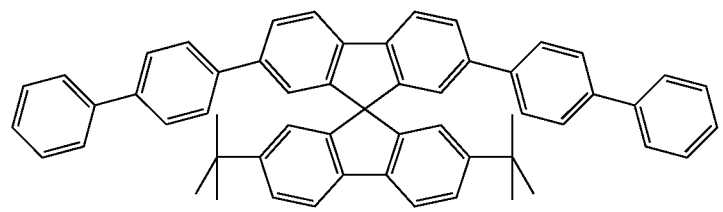

2,7-Bis(4-biphenyl-1-yl)-2',7'-di-tert-butyl-spiro-9,9'-bifluorene
HBM1

What is claimed is:

1. A compound of the formula (1)

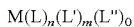

wherein a part-structure $M(L)_n$ is described by formula (2)

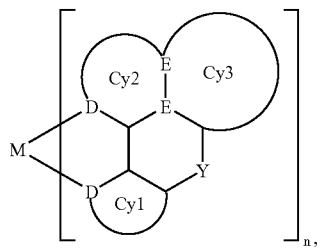

wherein the symbols and indices used are:
M at each instance is a transition metal ion;
Y is the same or different at each instance and is $C(R^1)_2$, C=O, C=NR$^1$, or C=C(R$^1$)$_2$;
D is a carbon atom in Cy1 and a nitrogen atom is Cy2;
E for each occurrence is C;
Cy1 is the same or different at each instance and is a six-membered monocyclic aryl ring which is bonded to the metal M via an atom D and which also has a single bond to the part-cycle Cy2 and a single bond to the Y group;
Cy2 is the same or different at each instance and is a six-membered heteroaryl ring containing one N atom and which is bonded via an atom D to the metal M and which also has a single bond to the cycle Cy1 and a common edge with the part-cycle Cy3;
Cy3 is the same or different at each instance and is a six-membered monocyclic aryl ring which has a single bond to the Y group and a common edge with the part-cycle Cy2;
R$^1$ is the same or different at each instance and is H or an aliphatic or aromatic hydrocarbon radical having from 1 to 20 carbon atoms;
n is 1, 2 or 3;
L' and L" are monoanionic, bidentate chelating ligands, and m and o are the same or different at each instance and are 0, 1 or 2.

2. A compound as claimed in claim 1, comprising a part-structure $M(L)_n$ described by the formula (2a):

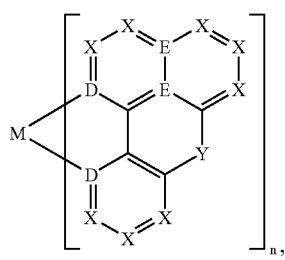

wherein:
M is Mo, W, Re, Ru, Os, Rh, Ir, Pd, Pt or Au;
X is CR;
R is the same or different at each instance and is H, F, Cl, Br, I, OH, NO$_2$, CN, a straight-chain, branched or cyclic alkyl or alkoxy group having from 1 to 20 carbon atoms, where one or more nonadjacent CH$_2$ groups may be replaced by —R$^1$C=CR$^1$—, —C≡C—, Si(R$^1$)$_2$, Ge(R$^1$)$_2$,Sn(R$^1$)$_2$, —O—, —S—, —NR$^1$—, —(C=O)—, —(C=NR$^1$)—, —P=O(R$^1$)— or —CONR$^1$— and where one or more hydrogen atoms may be replaced by F, or an aryl, heteroaryl, aryloxy or heteroaryloxy group which has from 1 to 14 carbon atoms and may be substituted by one or more nonaromatic R radicals, where a plurality of substituents R, both on the same ring and on different rings, may in turn form a further mono- or polycyclic, aliphatic or aromatic ring system.

3. A compound of claim 2, comprising at least one part-structure M(L), of the formula (2b) identical or different at each instance,

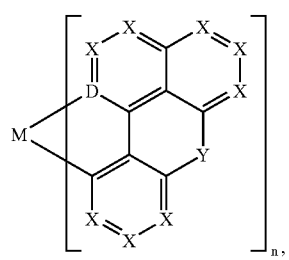

and further optionally comprising a part-structure $M(L')_m$ of the formula (3a), identical or different at each instance

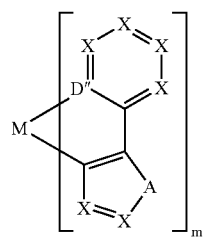

wherein:
D" is the same or different at each instance and is N or P; and
A is the same or different at each instance and is —CR=CR—, —N=CR—, —P=CR—, —N=N—, —P=N—, NR, PR, O, S, Se.

4. A compound of claim 3, wherein M is Rh, Ir, Pd or Pt.
5. A compound of claim 4, wherein n is 2 or 3.
6. A compound of claim 5, wherein D" is N.
7. A compound claim of claim 1, wherein Y is C(R$^1$)$_2$, C=O, or C=C(R$^1$)$_2$.
8. A compound of claim 2, wherein R is the same or different at each instance and is H, F, a straight-chain, branched or cyclic alkyl or alkoxy group having from 1 to 4 carbon atoms, where one or more hydrogen atoms may be replaced by F, or an aryl or heteroaryl group which has from 1 to 6 carbon atoms and may be substituted by one or more nonaromatic R radicals, where a plurality of substituents R, both on the same ring and on different rings, together may in turn form a further aliphatic or aromatic, mono- or polycyclic ring system.
9. A compound of claim 7, wherein Y is C(R1)2 and the carbon in the C9R1)2 is a spiro atom.

10. A compound of the formula (4)

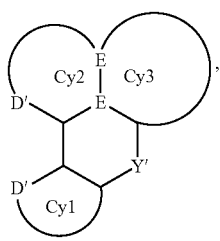
(4)

wherein:
E for each occurrence is C;
Cy1 is the same or different at each instance and is a six-membered monocyclic aryl ring and which also has a single bond to the part-cycle Cy2 and a single bond to the Y' group;
Cy2 is the same or different at each instance and is a six-membered heteroaryl ring containing one N atom and which also has a single bond to the cycle Cy1 and a common edge with the part-cycle Cy3;
Cy3 is the same or different at each instance and is a six-membered monocyclic aryl ring which has a single bond to the Y' group and a common edge with the part-cycle Cy2;
Y' is the same or different at each instance and is $C(R^1)_2$, $C=NR^1$, or $C=C(R^1)_2$;
D' is a carbon atom in Cy1 and a nitrogen atom in Cy2; and
R' is the same or different at each instance and is H or an aliphatic or aromatic hydrocarbon radical having from 1 to 20 carbon atoms.

11. A compound of claim 10, represented by formula (4a):

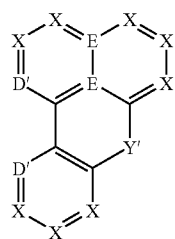
(4a)

wherein:
X is CR;
R is the same or different at each instance and is H, F, Cl, Br, I, OH, $NO_2$, CN, a straight-chain, branched or cyclic alkyl or alkoxy group having from 1 to 20 carbon atoms, where one or more nonadjacent $CH_2$ groups may be replaced by $-R^1C=CR^1-$, $-C\equiv C-$, $Si(R^1)_2$, $Ge(R^1)_2$, $Sn(R^1)_2$, $-O-$, $-S-$, $-NR^1-$, $-(C=O)-$, $-(C=NR^1)-$, $-P=O(R^1)-$ or $-CONR^1-$ and where one or more hydrogen atoms may be replaced by F, or an aryl, heteroaryl, aryloxy or heteroaryloxy group which has from 1 to 14 carbon atoms and may be substituted by one or more nonaromatic R radicals, where a plurality of substituents R, both on the same ring and on different rings, may in turn form a further mono- or polycyclic, aliphatic or aromatic ring system.

12. A process for preparing compound of the formula (1)

$$M(L)_n(L')_m(L'')_o \quad (1),$$

wherein a part-structure $M(L)_n$ is described by formula (2)

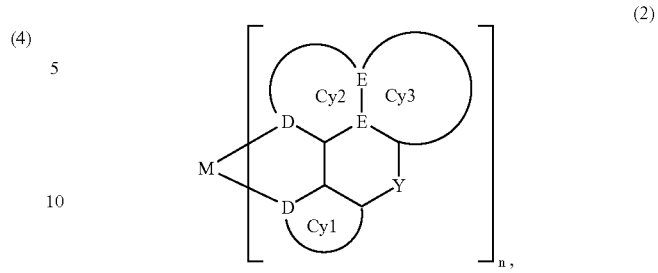
(2)

wherein the symbols and indices used are:
M at each instance is a transition metal ion;
Y is the same or different at each instance and is $C(R^1)_2$, $C=O$, $C=NR_1$ or $C=C(R^1)_2$,
D is a carbon atom in Cy1 and a nitrogen atom in Cy2;
E for each occurrence is C;
Cy1 is the same or different at each instance and is a six-membered monocyclic aryl ring which is bonded to the metal M via an atom D and which also has a single bond to the part-cycle Cy2 and a single bond to the Y group;
Cy2 is the same or different at each instance and is a six-membered heteroaryl ring containing one N atom and which is bonded via an atom D to the metal M and which also has a single bond to the cycle Cy1 and a common edge with the part-cycle Cy3;
Cy3 is the same or different at each instance and is a six-membered monocyclic aryl ring which has a single bond to the Y group and a common edge with the part-cycle Cy2;
$R^1$ is the same or different at each instance and is H or an aliphatic or aromatic hydrocarbon radical having from 1 to 20 carbon atoms;
n is 1, 2 or 3;
L' and L'' are monoanionic, bidentate chelating ligands, and
m and o are the same or different at each instance and are 0, 1 or 2, by reacting a compound of the formula (4)

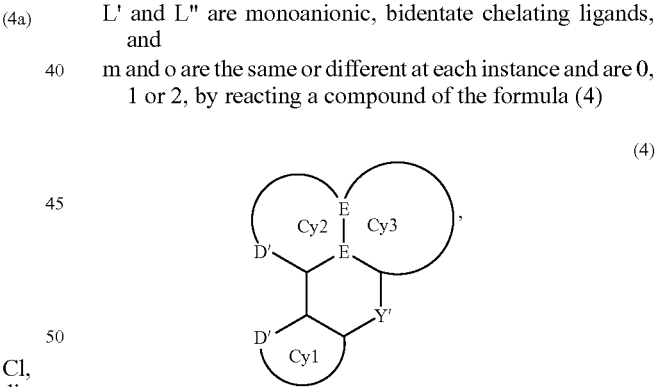
(4)

with metal alkoxides of formula (5), with metal ketoketonates of the formula (6) or mono- or polycyclic metal halides of the formula (7), (8) and (9)

$M(OR^1)_3$     Formula (5)

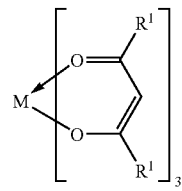
Formula (6)

-continued

MHal₃  Formula (7)

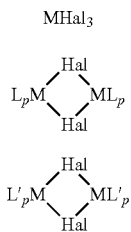

Formula (8)

Formula (9)

and further wherein:
D' is a carbon atom in Cy1 and a nitrogen atom in Cy2;
M(L)$_n$ is defined above
Y' is the same or different at each instance and is C(R¹)$_2$, C=O, C=NR$_1$ or C=C(R¹)$_2$,
p is 1 or 2; and
Hal is F, Cl, Br or I.

13. A process of claim 12, wherein a compound of formula (4) is reacted with iridium compounds which bear both alkoxide and/or halide and/or hydroxyl and ketoketonate radicals.

14. A compound of claim 1, wherein purity of said compound determined by means of ¹H NMR and/or HPLC is more than 99%.

15. A conjugated, part-conjugated or nonconjugated polymer or dendrimer containing one or more of the compounds as claimed in claim 1.

16. A conjugated, part-conjugated or nonconjugated polymer or dendrimer containing one or more of the compounds as claimed in claim 2, wherein at least one R is a bond to the polymer or dendrimer.

17. A polymer as claimed in claim 15, wherein the polymer is selected from the group of polyfluorenes, polyspirobifluorenes, polyparaphenylenes, polycarbazoles, polyvinylcarbazoles, polythiophenes, polyketones or copolymers thereof.

18. An electronic component comprising at least one compound as claimed in claim 1.

19. The electronic component of claim 18, wherein said component is an organic light-emitting diode (OLED), an organic integrated circuit (0-IC), an organic field-effect transistor (0-FET), an organic thin-film transistor (0-TFT), an organic solar cell (0-SC) or an organic laser diode (0-laser).

* * * * *